United States Patent [19]

Thomas et al.

[11] Patent Number: 5,770,202
[45] Date of Patent: Jun. 23, 1998

[54] CLONING AND SEQUENCING OF ALLERGENS OF DERMATOPHAGOIDES (HOUSE DUST MITE)

[75] Inventors: Wayne R. Thomas, Nedlands; Kaw-Yan Chua, Nollamara, both of Australia

[73] Assignees: The Institute for Child Health Research, West Perth, Australia; Immulogic Pharmaceutical Corporation, Waltham, Mass.

[21] Appl. No.: 461,809

[22] Filed: Jun. 5, 1995

Related U.S. Application Data

[63] Continuation of Ser. No. 945,288, Sep. 10, 1992, Pat. No. 5,433,948, which is a continuation-in-part of Ser. No. 580,655, Sep. 11, 1990, abandoned, which is a continuation-in-part of Ser. No. 458,642, Feb. 13, 1990, abandoned.

[51] Int. Cl.$^6$ .................................................. A61K 39/35
[52] U.S. Cl. ................................ 424/185.1; 424/192.1; 424/200.1; 424/275.1; 514/12; 530/350; 530/324; 530/325; 530/326; 530/327; 530/328; 530/329; 530/330
[58] Field of Search ............................ 424/185.1, 192.1, 424/200.1, 275.1; 514/12; 530/350, 858, 868, 324–330; 435/68.1, 69.3, 69.8, 71.1, 172.3, 252.3

[56] References Cited

U.S. PATENT DOCUMENTS

| 5,026,545 | 6/1991 | Saint-Remy et al. | 424/85.8 |
|---|---|---|---|
| 5,433,948 | 7/1995 | Thomas et al. | 424/185.1 |

FOREIGN PATENT DOCUMENTS

| A 50598/90 | 2/1990 | Australia . |
|---|---|---|
| A 71277/91 | 2/1991 | Australia . |

OTHER PUBLICATIONS

Chapman, et al. "II. Mite Alergens", The UCB Institute of Allergy, Bad Kreznach, Sep. 1–2, 1987;
Chua, et al., (1988) Chemical Abstracts, 105:148 (Abstract).
Chua, et al. (1990) "Expression of Dermatophagoides pteronyssinus Allergen, Der p. II. in Escherichia coli and the Binding Studies with Human IgE" *Int. Arch. Allergy Appl. Immunol.* 91(2):124–9 (Abstract).
Chua, et al, (1991) "IgE binding studies with large peptides expresed from der p II cDNA constructs", *Clinical and Experimental Allergy* 21:161–166.
Chua, et al. (1990) "Isolation of cDNA Coding for the Major Mite Allergen Der p II by IgE Plaque Immunoassay", *International Arch. of Allergy & Applied Immunol.*, 91:118–123.
Ford, et al. (1989) "The Spectrum of Low Molecular Weight House Dust Mite Allergens with Emphasis on Der p II" *Clin. and Experimental Allergy*, 20:27–31.
Greene, et al. (1992) "IgE Binding Structures of the Major House Dust Mite Allergen Der p I" *Molecular Immunology* 29(2):257–262.

Greene, et al. "IgE and EgG binding of peptides expressed from fragments fo cDNA encoding the major house dust mite allergen der p I" *The J. of Immunology* 147:3768–3773.
Gurka, et al, (1989) "Allergen–specific Human T Cell Clones: Derivation, Specificity, and Activation Requirements" *J Allergy Clin Immunol* 83(5):945–954.
Heymann, et al. Antigen Der f I from theust mite Dermatophagoides Farinae: structural comparison with Der p I from Dermatophagoides Pteronyssinus and Epitope Specificity . . . antibodies: *J. of Immunol.* 9:2841–47.
Krillis et al, (1984) "Antigens and Allergens from the Common House Dust Mite Dermatophagoides pteronyssinus" *J. of Aller. Clin, Immunol.* Aug. pp. 142–146.
Lamb, et al. (1988) "The use of nitrocellulose immunoblots for the analysis of antigen recognition by T Lymphocytes" *J. of Immun. Methods* 110(1):1–10.
Lamb, et al. (1989) "HLA class II restriction specificity of Dermatophagoides pp. reactive T lymphocyte clones that support IgE synthesis" *Clin. and Experim. Allergy*, 19:389–393.
O'Hehir, et al. (1989) "Clonal Analysis of the Cellular Immune Response to the House Dust Mite Dermatophagoides farinae" *Int. Arch. Allergy Appl. Immunol.*, 88:170–172.
Pierce, et al. (1986) "Molecular cloning fo Schistosoma" *Biochem. Genetics*, 108;191 (Abstract).
Rosenwasser, Lanny J., (1991) "Molecular Biology of Allergen Characterization" Post Graduate Education Course Syllabus, AAAI Meeting, Mar. 5, 1991.
Schad, V. et al. (1991) "The Potential Use of T Cell Epitopes to alter the Immune Response" *Immunology* 3:217–224.
Stewart, et al. (1987) "Immunogenicity and Tolerogenicity of a Major House Dust Mite Allergen, Der p I from Dermatophagoides pteronyssinus, in Mice and Rats" *Int. Arch. Allergy App. Immunol.* 83(1):44–51.
Stewart, et al.(1987) "In vitro translation of Messenger RNA from the House Dust Mite" *Int. Archs. Allergy Apl. Immunol.*, 83:384–389.

(List continued on next page.)

*Primary Examiner*—Laurie Scheiner
*Attorney, Agent, or Firm*—Lahive & Cockfield, LLP

[57] ABSTRACT

The present invention features isolated DNA encoding allergens of Dermatophagoides (house dust mites) particularly of the species *Dermatophagoides farinae* and *Dermatophagoides pteronyssinus*, which are protein allergens or peptides which include at least one epitope of the protein allergen. In particular, the invention provides DNA encoding the major *D. farinae* allergens, *Der f* I and *Der f* II and DNA encoding the major *D. pteronyssinus* allergens, *Der p* I and *Der p* II. The present invention further relates to proteins and peptides encoded by the isolated *D. farinae* and *D. pteronyssinus* DNA, including proteins containing sequence polymorphisms. In addition, the proteins or peptides encoded by the isolated DNA, their use a diagnostic and therapeutic reagents and methods of diagnosing and treating sensitivity to house dust mite allergens, are disclosed.

2 Claims, 29 Drawing Sheets

OTHER PUBLICATIONS

Stewart, et al. (1987) An Allergen and Antigenic Mapping Analysis of a Major Mite Allergen, Der p. I: Apr. 11–12, 1988, DPC First International Symposium, Laguna Niguel, California.

Stewart, et al (1987) [Abstracts from the Annual Metting], "The Physico–chemical Characterization of a Major Protein Allergen Der–P–I from the House Dust, Dermatophagoides pteronyssinus Amino Acid Analysis and Circular Dichroism Studies" *Int Arch Allergy Appl. Immunol* 82:(3–4) (Conference Paper).

Stewart, et al, "2. Epitope mapping analysis of the major mite allergens using synthetic peptides" Meeting on Sep. 1987, (see International Workshop Report, 1988) Mite Allergy conference, Bad Kreuznach.

Thomas, et al. (1988) "Cloning and Expression of DNA Coding for the Major House Dust Mite Allergen Der p I in *Escherichia Coli*" *Int. Archs. Allergy Appl. immun.* 85:127–129.

Thomas et al. "4. Expression of the house dust mite allergen Der p I in *E. coli*" Mite Allergy conference, BadKreuznach.

Tasieda. et al. "Isolation and Characterization of two allergens from Dermatophagoides farinae" *Chemical Abstracts*, 105:552 (abstract).

Thomas, et al., (1990) "Anlaysis and Expression of cDNA clones coding for house dust mite allergens" *Biochem. Genetics*, 113:179.

Thomas et al. "6 recombinant Mite Allergens", Proc. of Workshop XIV London Europe Acad. Allergy, Sep. 1989.

Tovey, et al. (1989) "Cloning and Sequencing of a cDNA Expressing a Recombinant House Dust Mite Protein that binds human IgE and corresponds to an important low molecular weight allergen" Brief Definition, J. of Exp. Med. 170(4):1457–62.

Trudinger, et al. (1991) "cDNA endocing the major mite allergen Der f II," *Clinical and Exper. Allergy* 24:33–37.

Van't Hof, et al. (1991) "Epitope Mapping of the dermatophagoides pteronyssinus house dust mite major allergen Der p II using overlapping synthetic peptides" *Molecular Immunolgy*, 28(11):1225–1232.

Yssel, et al. (1992) "T cell activation–inducing epitopes of the hous dust mite allergen Der p I" *J. of Immunology* 148:738–745.

Yssel, et al., "T Cell Activation by allergen derived synthetic peptides" Session 4: Immunity to Peptides, Sep. 24, 1990, Trinity College.

Yukki, et al. (1990) "Cloning and Sequencing of cDNA Corresponding to mite major allergen Der f II" *Jpn. J. Allergoi*, 39(6):557–561.

```
-23
AAA AAC CGA TTT TTG ATG AGT GCA GAA GCT TTT GAA CAC CTC AAA ACT      48
Lys Asn Arg Phe Leu Met Ser Ala Glu Ala Phe Glu His Leu Lys Thr
                            -1                      -10

CAA TTC GAT TTG AAT GCT GAA ACT AAC GCC TGC AGT ATC AAT GGA AAT      96
Gln Phe Asp Leu Asn Ala Glu Thr Asn Ala Cys Ser Ile Asn Gly Asn
 10                                          20

GCT CCA GCT GPA ATC GAT ILe ASP CGA CAA ATG ACT GTC ACT CCC ATT     144
Ala Pro Ala Glu Ile Asp Leu Arg Gln Met Arg Thr Val Thr Pro Ile
                     30                                       40

CGT ATG CAA GGA GGC TGT GGT TCA TGT TGG GCT TCT GGT GTT GCC         192
Arg Met Gln Gly Gly Cys Gly Ser Cys Trp Ala Phe Ser Gly Val Ala
                                      50

GCA ACT GAA TCA GCT TAT TTG GCT TTG GAT TGT CAA TCA CAC TTG GAT CTT 240
Ala Thr Glu Ser Ala Tyr Leu Ala Leu Asp Cys Gln Ser His Leu Asp Leu
         60                                      70

GCT GAA CAA CAA GAA TTA GTC GAT TGT GCT TCC CAA CAC CAC GGT TGT CAT GGT 288
Ala Glu Gln Gln Glu Leu Val Asp Cys Ala Ser Gln His His Gly Cys His Gly
                             80

GAT ACC ATT CCA CGT GGT GGG ATT GAA TAC ATC CAA CAT CAA AAT GGT GTC GTC 336
Asp Thr Ile Pro Arg Gly Gly Ile Glu Tyr Ile Gln His Gln Asn Gly Val Val
 90                                                             100

CAA GAA AGC TAC TAT TAT CGA TAC GTT GCA CGA GAA CAA GAA CAA TCA TGC CGA CGA 384
Gln Glu Ser Tyr Tyr Tyr Arg Tyr Val Ala Arg Glu Gln Glu Gln Ser Cys Arg Arg
             110                                                         120

CCA AAT GCA CAA CGT TTC GGT ATC TCA AAC TAT TGC CAA ATT TAC CCA          432
Pro Asn Ala Gln Arg Phe Gly Ile Ser Asn Tyr Cys Gln Ile Tyr Pro
                             130
```

Fig. 1A

```
CCA AAT GCA AAC AAA ATT CGT GAA GCT TTG GCT CAA ACC CAC AGC GCT    480
Pro Asn Ala Asn Lys Ile Arg Glu Ala Leu Ala Gln Thr His Ser Ala
            140                                 150

ATT GCC GTC ATT GGC ATC ATT GAT TTA GAC GCA TTC CGT CAT TAT        528
Ile Ala Val Ile Gly Ile Ile Asp Leu Asp Ala Phe Arg His Tyr
                    160

GAT GGC CGA ACA ATC ATT CAA CGC GAT AAT GGT TAC CAA CCA AAC TAT    576
Asp Gly Arg Thr Ile Ile Gln Arg Asp Asn Gly Tyr Gln Pro Asn Tyr
170                                         180

CAC GCT GTC AAC ATT GTT GGT TAC AGT AAC GCA CAA GGT GTC GAT TAT    624
His Ala Val Asn Ile Val Gly Tyr Ser Asn Ala Gln Gly Val Asp Tyr
                        190                                 200

TGG ATC GTA CGA AAC AGT TGG GAT ACC AAT TGG GGT GAT AAT GGT TAC    672
Trp Ile Val Arg Asn Ser Trp Asp Thr Asn Trp Gly Asp Asn Gly Tyr
                                210

GGT TAT TTT GCT GCC AAC ATC GAT TTG ATG ATT GAA GAA TAT CCA        720
Gly Tyr Phe Ala Ala Asn Ile Asp Leu Met Met Ile Glu Glu Tyr Pro
        220                 222

TAT GTT GTC ATT CTC TAAACAAAAAGACAATTTCTTATATGATTGTCACTAATTTATT    778
Tyr Val Val Ile Leu

TAAAATCAAAATTTTTAGAAAATGAATAAATTCATTCACAAAATTAAAAAAAAAAAAAAAAA    841
AAAAAAAAAAAAAAA 857
```

Fig. 1B

```
              1                                   10
Der p 1  Thr Asn Ala Cys Ser Ile Asn - Gly Asn Ala Pro
              *       *       *   *       *           *
Der f 1  Thr Ser Ala Cys Arg Ile Asn Ser Val Asn Val Pro

20
Der p 1  Ala Glu Ile Asp Leu Arg Gln Met
                  *       *       *
Der f 1  Ser Glu Leu Asp Leu Arg Ser Leu
```

Fig. 3

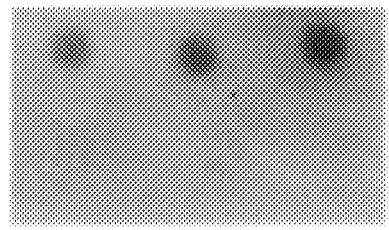 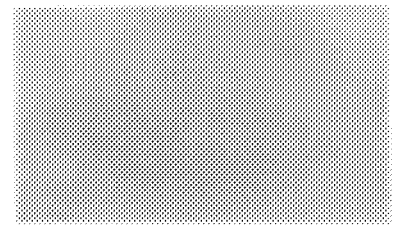
FIG. 4

```
CACAAATTCTTCTTTCTTCCTTACTACTGATCATTAATCTGAAAACAAACCAAACCAT
         -16

TCAAAATGATG TAC AAA ATT TTG TGT CTT TCA TTG GTC GCA GCC GTT
            Met Tyr Lys Ile Leu Cys Leu Ser Leu Val Ala Ala Val
            -1  1                             10

GCT CGT GAT CAA GTC GAT GTC AAA GAT TGT GCC AAT CAT GAA ATC AAA
Ala Arg Asp Gln Val Asp Val Lys Asp Cys Ala Asn His Glu Ile Lys

AAA GTT TTG GTA CCA GGA TGC CAT GGT TCA GAA CCA TGT ATC ATT CAT
Lys Val Leu Val Pro Gly Cys His Gly Ser Glu Pro Cys Ile Ile His
                    20                                       30

CGT GGT AAA CCA TTC CAA TTG GAA GCC GTT TTC GAA GCC AAC CAA AAC
Arg Gly Lys Pro Phe Gln Leu Glu Ala Val Phe Glu Ala Asn Gln Asn
                                40

ACA AAA ACG GCT AAA ATT GAA ATC AAA GCC TCA ATC GAT GGT TTA GAA
Thr Lys Thr Ala Lys Ile Glu Ile Lys Ala Ser Ile Asp Gly Leu Glu
            50                                       60
```

Fig. 7A

```
                                        70
GTT GAT GTT CCC GGT ATC GAT CCA AAT GCA TGC CAT TAC ATG AAA TGC
Val Asp Val Pro Gly Ile Asp Pro Asn Ala Cys His Tyr Met Lys Cys
            80                                      90
CCA TTG GTT AAA GGA CAA CAA TAT GAT ATT AAA TAT ACA TGG AAT GTT
Pro Leu Val Lys Gly Gln Gln Tyr Asp Ile Lys Tyr Thr Trp Asn Val
                        100                                 110
CCG AAA ATT GCA CCA AAA TCT GAA AAT GTT GTC GTC ACT GTT AAA GTT
Pro Lys Ile Ala Pro Lys Ser Glu Asn Val Val Val Thr Val Lys Val
                                    120
ATG GGT GAT GAT GGT GTT TTG GCC TGT ATT GCT ATT CAT GCT AAA
Met Gly Asp Asp Gly Val Leu Ala Cys Ile Ala Ile Thr His Ala Lys
    129
ATC CGC GAT TAAATCAAACAAAATTTATTGATTTTGTAATCACAAATGATTGATTTCTT
Ile Arg Asp

TCCAAAAAAAAATAAATAAATTTTGGGAATTC   581
```

Fig. 7B

Der p II  DQVDVKDCANHEIKKVLVPGCHGSEPCIIHRGKPF

*     * *     *

Der f II  DQVDVKD?ANNEIKKVMVDG?HGSDP?IIHRGKPF

* = NON HOMOLOGOUS RESIDUES.

Fig. 8

```
                                                                                                           -98
GAATTCCGTTTTCTTCCATCAAAATTAAAAATTCATCAAAA ATG AAA TTC GTT TTG GCC ATT    62
-90                                        Met Lys Phe Val Leu Ala Ile
                                           -80

GCC TCT TTG TTG GTA TTG AGC ACT GTT TAT GCT CGT CCA GCT TCA ATC AAA ACT   116
Ala Ser Leu Leu Val Leu Ser Thr Val Tyr Ala Arg Pro Ala Ser Ile Lys Thr
-70                                                  -60

TTT GAA GAA TTC AAA AAA GCC TTC AAC AAA TAT GCC ACC GTT GAA GAG GAA   170
Phe Glu Glu Phe Lys Lys Ala Phe Asn Lys Tyr Ala Thr Val Glu Glu Glu
    -50                                                   -40

GAA GTT GCC CGT AAA AAC TTT TTG GAA TCA TTG TCA AAA TAT GTT GAA GCT AAC AAA   224
Glu Val Ala Arg Lys Asn Phe Leu Glu Ser Leu Ser Lys Tyr Val Glu Ala Asn Lys
                                                                        -20

GGT GCC ATC AAC CAT TTG TCC GAT TTG TCA CTC AAA ATC GAA TTC AAA AAC CGT TAT   278
Gly Ala Ile Asn His Leu Ser Asp Leu Ser Leu Lys Ile Glu Phe Lys Asn Arg Tyr
                              -30                       -10

TTG ATG AGT GCT GAA GCT TTT GAA CAA CTC CAA ACT CAA TTC GAT TTG AAT GCC   332
Leu Met Ser Ala Glu Ala Phe Glu Gln Leu Gln Thr Gln Phe Asp Leu Asn Ala
-1  1                                           10

GAA ACA AGC GCT TGC CGT ATC AAT TCG GTT AAC GTT CCA TCG GAA TTG GAT TTA   386
Glu Thr Ser Ala Cys Arg Ile Asn Ser Val Asn Val Pro Ser Glu Leu Asp Leu
        20                                          30

CGA TCA CTG CGA ACT GTC ACT CCA ATC CGT ATG CAA GGA GGC TGT GGT TCA TGT   440
Arg Ser Leu Arg Thr Val Thr Pro Ile Arg Met Gln Gly Gly Cys Gly Ser Cys
                 40                                              50

TGG GCT TTC TCT GGT GTT GCC GCA ACT GAA TCA GCT TAT TTG GCC TAC CGT AAC   494
Trp Ala Phe Ser Gly Val Ala Ala Thr Glu Ser Ala Tyr Leu Ala Tyr Arg Asn
```

Fig. 10A

```
ACG TCT TTG GAT CTT TCT GAA CAG CTC GTC GAT TGC GCA TCT CAA CAC GGA   548
Thr Ser Leu Asp Leu Ser Glu Gln Leu Val Asp Cys Ala Ser Gln His Gly
                         60              70
                                 80

TGT CAC GGC GAT ACA ATA CCA AGA GGC ATC GAA TAC ATC CAA AAT GGT GTC   602
Cys His Gly Asp Thr Ile Pro Arg Gly Ile Glu Tyr Ile Gln Asn Gly Val
 90                              100

GTT GAA AGA AGC TAT CCA TAC GTT GCA GAA CGA CAA CGA TGC CGA CGA CCA   656
Val Glu Arg Ser Tyr Pro Tyr Val Ala Glu Arg Gln Arg Cys Arg Arg Pro
        110

AAT TCG CAA CAT TAC GGT ATC TCA AAC TAC TGC CAA ATT TAT CCA CCA GTG   710
Asn Ser Gln His Tyr Gly Ile Ser Asn Tyr Cys Gln Ile Tyr Pro Pro Val
                130                              140

AAA CAA ATC CGT GAA GCT TTG AGA ACT CAA ACA CAC GCT ATT GCC GTC ATT ATT   764
Lys Gln Ile Arg Glu Ala Leu Arg Thr Gln Thr His Ala Ile Ala Val Ile Ile
                        150                                  160

GGC ATC AAA GAT GGT TAT CAA CAT TAT GAT CAT CAT GCC GTC AAC ATT GTC GGA   818
Gly Ile Lys Asp Gly Tyr Gln Pro Asn Tyr Asp His His Ala Val Asn Ile Gly
                                170

CAT GAC AAT GGT TAT GAC GAC GAT TAT TGG ATC GTA CGA AAC AGT TGG GAT ACT ACC TGG   872
His Asp Asn Gly Tyr Asp Asp Asp Tyr Trp Ile Val Arg Asn Ser Trp Asp Thr Thr Trp
180                                              190                   210

AGT ACA CAA GGC GAC GAC TAT TGG ATC GTA CGA AAC AGT TGG GAT ACT ACC TGG   926
Ser Thr Gln Gly Asp Asp Tyr Trp Ile Val Arg Asn Ser Trp Asp Thr Thr Trp
        200

GGA GAT AGC GGA TAC GGA TAT TTC CAA GCC GGA AAC CTC ATG ATG ATC GAA   980
Gly Asp Ser Gly Tyr Gly Tyr Phe Gln Ala Gly Asn Leu Met Met Ile Glu
        220         223

CAA TAT CCA TAT GTT GTA ATC ATG TGAACATTGAAAATTGAATATATTTATTTGTTTCAAAAT  1044
Gln Tyr Pro Tyr Val Val Ile Met
AAAACAACTACTCTTGCGAGTATTTTTACTCGGAATTC 1084
```

Fig. 10B

```
                    10        20        30        40        50        60
Der p 1    TNACSING*NAPAEIDLRQMRTVTPIRMQGGCGSCWAFSGVAATESAYLAHRNQSLDLAEQE
Der f 1    .S..R..SV.V.S.L...SL..............................Y..T....S...
                                       ▲   ▲▲▲

70     80        90       100       110       120
Der p 1    LVDCASQHGCHGDTIPRGIEYIQHNGVVQESYYRYVAREQSCRRPNAQRFGISNYCQIYPPN
Der f 1    .......................Q....E.RS.P......R.....S.HY...........D 130       140       150       160       170       180
Der p 1    ANKIREALAQTHSAIAVIIGIKDLDAFRHYDGRTIIQRDNGYQPNYHAVNIVGYSNAQGVDY
Der f 1    VKQ.....T...T...........R..Q.........H................GST..D..
                                                         ▲

190       200       210       220
Der p 1    WIVRNSWDTNWGDNGYGYFAANIDLMMIEEYPYVVIL
Der f 1    .........T...S.....Q.GNN.....Q......M
               ▲▲▲
```

Fig. 11

```
Cathepsin H   MWTALPLLCAGAWLLSAGATA------------------------ELTY-NA-IEKFH---FTSWMKQHQKTY-SS-
Cathepsin L   MTPLLLAVICLGTALA---------------------------TPKFDQ-TF-NAQWH-----QWKSTHRRLY-GT-
Papain        MAMIPSISKLLFVAICLFVYMGLSFG-----------DFSIVGYSQNDLTS-TE-RLIQL---FESWMLKHNKIYKNI-
Aleurain      MAHARVLLALAVLATAAVAYASSSSFADSNPIRPVTDRAASTLESAVLGALGRTRHALRFARFAVRYGKSYESA-
CP1           MKVILLFVLAVFTVF------------------VSSRGIPPEEQ-SQ-FLEFQ---DKFNKKYSHEEY-LE-
CP2           MRLLVFLILLIFVNFSFA----------------NVRPNGRRFS-ES-QYRTA---FTEWTLKFNRQY-SS-
Cathepsin B   MWWSLIPLSCLLALTSA-----------------------------HDK----PS-
CTLA-2α       MVSICEQKLQHFSAVFLLILCLGMMSA------------APPPDPSLDNEWKTKFAKAYNLN-
CTLA-2β       MVSICEQKLQHFSAVFLLILCLGMMSA------------APSPDPSLDNEWKEWKTTFAKAYSLD-
MCP           NLLLAVLCLGTALA------------------------TPKFDQTFSAEWHQWKSTHRRLY-GT-
Der f I       MKFVLAIASLLVLSTVYA----------------------RPASIKTFEEFKKAFNKNYATVE
                                                               **    *   *
```

Fig. 12A

```
Cathepsin H   REYSHRLQVFANNWRKIQAHN--QRN--HTFKMG--LNQFSDMSFAEIKIKYL-WSE-PQNCS--AT-KS--NYL--RGTGP
Cathepsin L   NEEEWRRAVWEKNMRMIQIHNGEYSNGKHGFIHE--MNAFGDMTNEEFRQIVN-GYR-HQKHK--KG-RL--FQE--PLMLQ
Papain        DEKIYRFEIFKDNLKYIDETN--KKN--NSYWLG--LNVFADMSNDEFKEKYT-GSI-AGNYT--TTELSYEEVL-NDGDVN
Aleurain      AEVRRRFRIFSESLEEVRSTN--RKG--LPYRLG--INRFSDMSWEEFQATRL-GA--AQTCS--ATLAG--NHL-MRDAAA
CP1           RFEIFKSNLGKIEELNLIAIN--HKA--DT-KFG--VNKFADLSSDEFKNYYLNNKEAIFTDD--LP-VA--DYLDDEFINS
CP2           SEFSNRYSIFKSNMDYVDNWN-SKGD--SQTVLG--LNNFADITNEEYRKTYL-GTR-VNAHSYNGYDGR--EVLNVEDLQT
Cathepsin B   ---FHPLS---DDM--INYIN--KQN--TTWQAG--RN-EYNV-DISYLKKPC-GTV-LGGPK--LP-ER--VGF--SEDIN
CTLA-2α       NEERHRRLVWEENKKKIEAHNADYEQGKTSFYMG--LNQFSDLTPEEFKTNCY-GNSLNRGEM
CTLA-2β       DEERHRRLMWEENKKKIEAHNADYERGKTSFYMG--LNQFSDLTPEEFRTNCC-GSSMCRGEM
MCP           NEEEWRRAIWEKNMRMIQLHNGEYSNGQHGFSME--MNAFGDMTNEEFRQVVN-GYRHQKHKK
Der p I                                                 --KNRFL-MS-AEAFEH-L-KTQFRLNAE
Actinidin                   LRFIDEHNAD-TNR--SYKVG--LNQFADLTGEEFRSTYL-G
Der f I       EEEVARKN-FLESLKYVEA-NKGAINHLSDLSLDEFKNRYL-MS-AEAFEQ-L-KTQFDLNAE
              **  *       *            *        * *** ** **  *    *
              *   *                                        *
```

Fig. 12B

```
GAT CAA GTC GAT GTT AAA GAT TGT GCC AAC AAT GAA ATC AAA AAA GTA ATG     51
Asp Gln Val Asp Val Lys Asp Cys Ala Asn Asn Glu Ile Lys Lys Val Met
                    20                      10
                                                          30
GTC GAT GGT TGC CAT GGT TCT GAT CCA TGC ATC ATC CAT CGT GGT AAA CCA    102
Val Asp Gly Cys His Gly Ser Asp Pro Cys Ile Ile His Arg Gly Lys Pro

TTC ACT TTG GAA GCC TTA TTC GAT GCC AAC CAA AAC ACT AAA ACC GCT AAA    153
Phe Thr Leu Glu Ala Leu Phe Asp Ala Asn Gln Asn Thr Lys Thr Ala Lys
                            40                              50

ACT GAA ATC AAA GCC AGC CTC GAT GGT CTT GAA ATT GAT GTT CCC GGT ATT    204
Thr Glu Ile Lys Ala Ser Leu Asp Gly Leu Glu Ile Asp Val Pro Gly Ile
            70                              80

GAT ACC AAT GCT TGC CAT TTT ATG AAA TGT CCA TTG GTT AAA GGT CAA CAA    255
Asp Thr Asn Ala Cys His Phe Met Lys Cys Pro Leu Val Lys Gly Gln Gln

TAT GAT GCC AAA TAT ACA TGG AAT GTG CCG AAA ATT GCA CCA AAA TCT GAA    306
Tyr Asp Ala Lys Tyr Thr Trp Asn Val Pro Lys Ile Ala Pro Lys Ser Glu
                90                                      100

AAC GTT GTC GTT ACA GTC AAA CTT GTT GGT GAT AAT GGT GTT TTG GCT TGC    357
Asn Val Val Val Thr Val Lys Leu Val Gly Asp Asn Gly Val Leu Ala Cys
                        110

GCT ATT GCT ACC CAC GCT AAA GCT AAA ATC CGT GAT TAAAAAAAAATAATGAAAATT  414
Ala Ile Ala Thr His Ala Lys Ala Lys Ile Arg Asp
120                                             129

TTCACCAACATCGAACAAAATTCAATAACAAAATTGAATCAAAAACGGAATTCCAAGCTGAGCGC     481

CGGTCGCTAC                                                             491
```

```
Dp II:                                                                                           63
        CACAAATTCTTCTTTCTTCCTTACTACTGATCATTAATCTGAAAACAAACCAAACAAACCAT
                        -16                            -10

Dp II:  TCAAAATGATG TAC AAA ATT TTG TGT CTT TCA TTG TTG GTC GCA GCC GTT    113
                    Met Tyr Lys Ile Leu Cys Leu Ser Leu Leu Val Ala Ala Val
                    -1   1

Dp II:  GCT CGT GAT CAA GTC GAT GTC AAA GAT TGT GCC AAT CAT GAA ATC AAA    161
        Ala Arg Asp Gln Val Asp Val Lys Asp Cys Ala Asn His Glu Ile Lys

Df II:  ... ... ... ... ... ... ... ... ..T ... ... ..C A.. ... ... ...     42
                                                        Asn
                                                        30

Dp II:  AAA GTT TTG GTA CCA GGA TGC CAT GGT TCA GAA CCA TGT ATC ATT CAT    209
        Lys Val Leu Val Pro Gly Cys His Gly Ser Glu Pro Cys Ile Ile His
              20

Df II:  ... ..A A.. ..C GAT ... ... ... ... ... ..T ... ... ..C ... ...     90
                        Met                            Asp
                        Asp

Dp II:  CGT GGT AAA CCA TTC CAA TTG GAA GCC GTT TTC GAA GCC AAC CAA AAC    257
        Arg Gly Lys Pro Phe Gln Leu Glu Ala Val Phe Glu Ala Asn Gln Asn
                                        40

Df II:  ... ... ... ... ... ACT ... ... ... ... ... T.A ... ..T ... ...    138
                             Thr                      Leu     Asp
```

| | | | | | | | | | | | | |
|---|---|---|---|---|---|---|---|---|---|---|---|---|
| | | | 50 | | | | | | 60 | | | |
| Dp II: | ACA | AAA | ACG | GCT | AAA | ATT | GAA | ATC | GAT | GGT | TTA | GAA | 305 |
| | Thr | Lys | Thr | Ala | Lys | Ile | Glu | Ile | Asp | Gly | Leu | Glu | |
| Df II: | ..T | ... | ... | ..C | ... | ..C | ... | AGC | C.. | ... | ... | C.T | 186 |
| | | | | | | Thr | | Leu | | | | | |
| | | | | | | 70 | | | | | | | |
| Dp II: | GTT | GAT | GTT | CCC | GGT | ATC | GAT | CCA | AAT | GCA | TGC | CAT | 353 |
| | Val | Asp | Val | Pro | Gly | Ile | Asp | Pro | Asn | Ala | Cys | His | |
| Df II: | A.. | ... | ... | ... | ... | ..T | ... | A.C | ... | ..T | ... | .TT | 234 |
| | Ile | | | | | | | Thr | | | | Phe | |
| | 80 | | | | | | | | | 90 | | | |
| Dp II: | CCA | TTG | GTT | AAA | GGA | CAA | CAA | TAT | GAT | ATT | AAA | TAT | 401 |
| | Pro | Leu | Val | Lys | Gly | Gln | Gln | Tyr | Asp | Ile | Lys | Tyr | |
| Df II: | ... | ... | ... | ... | ... | ... | ... | ... | ... | ... | ... | ... | 282 |
| | | | | | | | | | | | | | |
| | | | | | 100 | | | | | | 110 | | |
| Dp II: | CCG | AAA | ATT | GCA | CCA | AAA | GGA | CAA | TCT | GAA | AAT | GTT | 449 |
| | Pro | Lys | Ile | Ala | Pro | Lys | Gly | Gln | Ser | Glu | Asn | Val | |
| Df II: | ... | ... | ... | ... | ... | ... | ... | ... | ... | ..T | ..A | ..C | 330 |
| | | | | | | | | | | | | Leu | |

Fig. 16B

```
Dp II:   ATG GGT GAT GAT GGT GTT TTG GCC TGT GCT ATT GCT ACT CAT GCT AAA    497
         Met Gly Asp Asp Gly Val Leu Ala Cys Ala Ile Ala Thr His Ala Lys
                                    120

Df II:   G.T ... ... A.. ... ... ..T .. ...C ..C ... ... ..C ... ... ...    378
         Val

Dp II:   ATC CGC GAT TAA ATCAAACAAAATTTATTGATTTTGTAATCACAAATGATTGATTTTCTT    557
         Ile Arg Asp END
             129

Df II:   ... ..T ... ... .AA ...A ...TAAATA...AAA.T.TCA.CA.C.CGAAC.AAA.TCA    438

Dp II:   TCCAAAAAAAAAATAAATTTGGGAATTC                                       591

Df II:   ATA.CC....TTTG..TC....AC____GGAATTC                                469
```

Fig. 16C

|  |  | 10 | 20 | 30 | 40 | 50 | 60 |
|---|---|---|---|---|---|---|---|
| Der p I | (a) | TNACSINGNA | PAEIDLRQMR | TVTPIRMQGG | CGSCWAFSGV | AATESAYLAH | RNQSLDLAEQ |
| Der p I | (b) | ---------- | ---------- | ---------- | ---------- | -------Y-- | ---------- |
| Der p I | (c) | ---------- | ---------- | ---------- | ---------- | -------Y-- | ---------- |
| Der p I | (d) | ---------- | ---------- | ---------- | ---------- | ---------- | ---------- |

|  |  | 70 | 80 | 90 | 100 | 110 | 120 |
|---|---|---|---|---|---|---|---|
| Der p I | (a) | ELVDCASQHG | CHGDTIPRGI | EYIQHNGVVQ | ESYYRYVARE | QSCRRPNAQR | FGISNYCQIY |
| Der p I | (b) | ---------- | ---------- | ---------- | ---------- | ---------- | ---------- |
| Der p I | (c) | ---------- | ---------- | K--------- | ---------- | ---------- | ---------- |
| Der p I | (d) | ---------- | ---------- | ---------- | ---------- | ---------- | ---------- |

|  |  | 130 | 140 | 150 | 160 | 170 | 180 |
|---|---|---|---|---|---|---|---|
| Der p I | (a) | PPNANKIREA | LAQTHSAIAV | IIGIKDLDAF | RHYDGRTIIQ | RDNGYQPNYH | AVNIVGYSNA |
| Der p I | (b) | ---V------ | ---------- | ---------- | ---------- | ---------- | ---------- |
| Der p I | (c) | ---V------ | ---------- | ---------- | ---------- | ---------- | ---------- |
| Der p I | (d) | ---------- | --T------- | ---------- | ---------- | -------Y-- | ---------- |
| Der p I | (e) | ---------- | ---------- | ---------- | ---------- | -------Y-- | ---------- |

|  |  | 190 | 200 | 210 | 220 |  |  |
|---|---|---|---|---|---|---|---|
| Der p I | (a) | QGVDYWIVRN | SWDTNWGDNG | YGYFAANIDL | MMIEEYPYVV | IL |  |
| Der p I | (b) | ---------- | ---------- | ---------- | ---------- | -- |  |
| Der p I | (c) | ---------- | ---------- | ---------- | --Q------- | -- |  |
| Der p I | (d) | ---------- | ---------- | ---------- | ---------- | -- |  |
| Der p I | (e) | ---------- | ---------- | ---------- | ---------- | -- |  |

Fig. 18

```
                    10         20         30         40         50
Der p II  (c) DQVDVKDCANHEIKKVLVPGCHGSEPCIIHRGKPFQLEAVFEANQNTKTAK
          (1) .............H....L.P......E........Q...V.E....T...
          (2) .............H....L.P......E........Q...V.E....S...
Der f II      ................N....M.D......D........T...L.D....T...

60         70         80         90         100
Der p II  (c) IEIKASIDGLEVDVPGIDPNACHYMKCPLVKGQQYDIKYTWNVPKIAPKSE
          (1) ......I..........P.....YM........I................
          (2) ......I..........P.....YM........I................
Der f II      ......L..........T.....FM........A................
                                        V                I 110        120
Der p II  (c) NVVVTVKVMGDDGVLACAIATHAKIRD
          (1) .......VM.DD......A....I..
          (2) .......VM.ND......A....L..
Der f II      .......LV.DN......A....I..
                      I           G
```

Fig. 19

```
                    10         20         30         40         50         60
pFL1    DQVDKDCANNEIKKVMVPGCHGSEPCIIHRGKPFTLEALFDANQNTKTAKIEIKASLDGLE
pFL2    ..........N.................................I.I............
MT  3   ..........N.................................I.T............
MT  5   (1-92)....S.................................I.I............
MT18    (1-84)....N.................................I.I............
MT16    (1-70)....N...............................T.I............

70         80         90        100        110        120        130
pFL1    IDVPGIDTNACHFVKCPLVKGQQYDIKYTWNVPKIAPKSENVVVTVKLIGDNGVLACAIATHAKIRD
pFL2    .............M...........A................V......................
MT  3   .............M.............................V......................
MT  5   .............M...........A........................................
MT18    .............M.....................I..............................
```

Fig. 20

```
GAATTCCTTT TTTTTTCTTT CTCTCTCTAA AATCTAAAAT CCATCCAAC ATG AAA ATT      58
                                                       Met Lys Ile
                                                        -98

GTT TTG GCC ATC GCC TCA TTG TTG GCA TTG AGC GCT GTT TAT GCT CGT       106
Thr Leu Ala Ile Ala Ser Leu Leu Ala Leu Ser Ala Val Tyr Ala Arg
-95                 -90                 -85                 -80

CCA TCA TCG ATC AAA ACT TTT GAA GAA TAC AAA AAA GCC TTC AAC AAA       154
Pro Ser Ser Ile Lys Thr Phe Glu Glu Tyr Lys Ala Phe Asn Lys
            -75                 -70                 -65

AGT TAT GCT ACC TTC GAA GAT CAA GAA GCT GCC CGT AAA AAC CAT TTG       202
Ser Tyr Ala Thr Phe Glu Asp Gln Glu Ala Ala Arg Lys Asn His Leu
        -60                 -55                 -50

GAA TCA GTA AAA TAT GTT CAA TCA AAT GGA GGT GCC ATC ATC TTT TTG       250
Glu Ser Val Lys Tyr Val Gln Ser Asn Gly Gly Ala Ile Asn Phe Leu
    -45                 -40                 -35

TCC GAT TTG TCG TTG GAT GAA CGA TTT AAA AAC CGA TTT TTG ATG AGT GCA   298
Ser Asp Leu Ser Leu Asp Glu Arg Phe Lys Asn Arg Phe Leu Met Ser Ala
-30                 -25                 -20

GAA GCT TTT GAA CAC CTC AAA CTC AAA ACT CAA TTC GAT TTG AAT GCT GAA ACT   346
Glu Ala Phe Glu His Leu Lys Leu Lys Thr Gln Phe Asp Leu Asn Ala Glu Thr
-15                 -10                 -5                  -1  1

AAC GCC TGC AGT ATC AAT GGA AAT GCT CCA GCT GAA ATC GAT TTG CGA       394
Asn Ala Cys Ser Ile Asn Gly Asn Ala Pro Ala Glu Ile Asp Leu Arg
            5                   10                  15
```

```
CAA ATG CGA ACT GTC ACT CCC ATT CGT ATG CAA GGA GGC TGT GGT TCA    442
Gln Met Arg Thr Val Thr Pro Ile Arg Met Gln Gly Gly Cys Gly Ser
                    20              25              30

TGT TGG GCT TTC TCT GGT GTT GCC ACT GAA TCA GCT TAT TTG GCT        490
Cys Trp Ala Phe Ser Gly Val Ala Thr Glu Ser Ala Tyr Leu Ala
        35              40              45

CAC CGT AAT CAA CAA TCA TTG GAT CTT GCT GAA CAA GAA TTA GTC GAT TGT  538
His Arg Asn Gln Gln Ser Leu Asp Leu Ala Glu Gln Glu Leu Val Asp Cys
50              55              60              65

GCT TCC CAA CAC CAC GGT CAT GGT GAT ACC ATT CCA CGT GGT ATT GAA    586
Ala Ser Gln His His Gly His Gly Asp Thr Ile Pro Arg Gly Ile Glu
            70              75              80

TAC ATC CAA CAT GGT AAT GGT GTC CAA GAA AGC TAC TAT CGA TAC GTT    634
Tyr Ile Gln His Gly Asn Gly Val Gln Glu Ser Tyr Tyr Arg Tyr Val
                85              90              95

GCA CGA GAA CAA GAA TCA TGC CGA CCA CGA CAA AAT GCA CGT TTC GGT ATC 682
Ala Arg Glu Gln Glu Ser Cys Arg Pro Arg Gln Asn Ala Arg Phe Gly Ile
        100             105             110

TCA AAC TAT TGC CAA ATT TAC CCA CCA AAT GCA AAC CCA AAT GCA AAT GCA AAA ATT CGT GAA  730
Ser Asn Tyr Cys Gln Ile Tyr Pro Pro Asn Ala Asn Pro Asn Ala Lys Ile Arg Glu
115             120             125
```

```
GCT TTG GCT CAA ACC CAC AGC GCT ATT ATT GGC ATC AAA    778
Ala Leu Ala Gln Thr His Ser Ala Ile Ile Gly Ile Lys
130                 135                 140         145

GAT TTA GAC GCA TTC CGT CAT TAT GAT GGC GTC ACA ATC ATT CAA CGC    826
Asp Leu Asp Ala Phe Arg His Tyr Asp Gly Val Thr Ile Ile Gln Arg
            150                 155                 160

GAT AAT GGT TAC CAA CCA AAC TAT CAC GCT GTC AAC ATT GTT GGT TAC    874
Asp Asn Gly Tyr Gln Pro Asn Tyr His Ala Val Asn Ile Val Gly Tyr
        165                 170                 175

AGT AAC GCA CAA GGT GTC GAT TAT TGG ATC GTA CGA AAC AGT TGG GAT    922
Ser Asn Ala Gln Gly Val Asp Tyr Trp Ile Val Arg Asn Ser Trp Asp
    180                 185                 190

ACC AAT TGG GGT GAT AAT GGT TAC GGT TAT TTT GCT GCC AAC ATC GAT    970
Thr Asn Trp Gly Asp Asn Gly Tyr Gly Tyr Phe Ala Ala Asn Ile Asp
195                 200                 205

TTG ATG ATG ATT GAA GAA TAT CCA TAT GTT GTC ATT CTC TAAACAAAAA    1019
Leu Met Met Ile Glu Glu Tyr Pro Tyr Val Val Ile Leu
210                 215                 220

GACAATTTCT TATATGATTG TCACTAATTT ATTTAAAATC AAAATTTTTA GAAAATGAAT    1079

AAATTCATTC ACAAAAATTA AAAAAAAAAA AAAAAAAAAA AAAAAAAAAA AAAAAAAAAA    1139

AAAAAAAAAA AAAAAAAAAA AAAAAAAAAA AAA                                1172
```

Fig. 21C

CLONING AND SEQUENCING OF ALLERGENS OF DERMATOPHAGOIDES (HOUSE DUST MITE)

RELATED APPLICATIONS

This application is a continuation application of Ser. No. 07/945,288 filed on Sep. 10, 1992, now U.S. Pat. No. 5,433,948, which in turn is a continuation-in-part application of Ser. No. 580,655 filed on Sep. 11, 1990, now abandoned, which in turn is a continuation-in-part application of Ser. No. 458,642 filed on Feb. 13, 1990, now abandoned. This application also claims priority to an international application, PCT/AU91/00417 filed on Sep. 10, 1991. The contents of all of the aforementioned application (s) are hereby incorporated by reference.

BACKGROUND

Recent reports have documented the importance of responses to the Group I and Group II allergens in house dust mite allergy. For example, it has been documented that over 60% of patients have at least 50% of their anti-mite antibodies directed towards these proteins (Lind, P. et al., *Allergy*, 39:259–274 (1984); van der Zee, J. S. et al., *J Allergy Clin. Immunol.*, 81:884–896 (1988)). It is possible that children show a greater degree of reactivity (Thompson, P. J. et al., *Immunology* 64:311–314 (1988)). Allergy to mites of the genus Dermatophagoides (D.) is associated with conditions such as asthma, rhinitis and ectopic dermatitis. Two species, *D. pteronyssinus* and *D. farinae*, predominate and, as a result, considerable effort has been expended in trying to identify the allergens produced by these two species. *D. pteronyssinus* mites are the most common Dermatophagoides species in house dust in Western Europe and Australia. The species *D. farinae* predominates in other countries, such as North America and Japan (Wharton, G. W., *J. Medical Entom*, 12:577–621 (1976)). It has long been recognized that allergy to mites of this genus is associated with diseases such as asthma, rhinitis and atopic dermatitis. It is still not clear what allergens produced by these mites are responsible for the allergic response and associated conditions.

SUMMARY OF THE INVENTION

The present invention relates to isolated DNA which encodes a protein allergen of Dermatophagoides ((D.) house dust mite) or a peptide which includes at least one epitope of a protein allergen of a house dust mite of the genus Dermatophagoides. It particularly relates to DNA encoding major allergens of the species *D. farinae*, designated *Der f* I and *Der f* II, or portions of these major allergens (i.e., peptides which include at least one epitope of *Der f* I or of *Der f* II). It also particularly relates to DNA encoding major allergens of *D. pteronyssinus*, designated *Der p* I and *Der p* II, or portions of these major allergens (i.e., peptides which include at least one epitope of *Der p* I or of *Der p* II).

The present invention further relates to proteins and peptides encoded by the isolated Dermatophagoides (e.g., *D. farinae*, *D. pteronyssinus*) DNA including proteins containing sequence polymorphisms. Several nucleotide and resulting amino acid sequence polymorphisms have been discovered in the *Der p* I, *Der p* II and *Der f* II allergens. All such nucleotide variations and proteins, or portions thereof, containing a sequence polymorphism are within the scope of the invention.

Peptides of the present invention include at least one epitope of a *D. farinae* allergen (e.g., at least one epitope of *Der f* I or *Der f* II) or at least one epitope of a *D. pteronyssinus* allergen (e.g., at least one epitope of *Der p* I or of *Der p* II). It also relates to antibodies specific for *D. farinae* proteins or peptides and to antibodies specific for *D. pteronyssinus* proteins or peptides.

Dermatophagoides DNA, proteins and peptides of the present invention are useful for diagnostic and therapeutic purposes. For example, isolated *D. farinae* proteins or peptides can be used to detect sensitivity in an individual to house dust mites and can be used to treat sensitivity (reduce sensitivity or desensitize) in an individual, to whom therapeutically effective quantities of the *D. farinae* protein or peptide is administered. For example, isolated *D. farinae* protein allergen, such as *Der f* I or *Der f* II, can be administered periodically, using standard techniques, to an individual in order to desensitize the individual. Alternatively, a peptide which includes at least one epitope of *Der f* I or of *Der f* II can be administered for this purpose. Isolated *D. pteronyssinus* protein allergen, such as *Der p* I or *Der p* II, can be administered as described for *Der f* I or *Der f* II. Similarly, a peptide which includes at least one *Der p* I epitope or at least one *Der p* II epitope can be administered for this purpose. A combination of these proteins or peptides (e.g., *Der f* I and *Der f* II; *Der p* I and *Der p* II; or a mixture of both *Der f* and *Der p* proteins) can also be administered. The use of such isolated proteins or peptides provides a means of desensitizing individuals to important house dust mite allergens.

BRIEF DESCRIPTION OF THE DRAWINGS

FIG. 1A and 1B show the nucleotide and predicted amino acid sequence of cDNA λgt11 p1(13T). Numbers to the right are nucleotide positions whereas numbers above the sequence are amino acid positions. Positive amino acid residue numbers correspond to the sequence of the mature excreted *Der p* I beginning with threonine. Negative sequence numbers refer to the proposed transient pre- and preproenzyme forms of *Der p* I. The arrows indicate the beginning of the proposed proenzyme sequence and the mature *Der p* I, respectively. Residues −15 to −13 enclosed by an open box make up the proposed cleavage for the proenzyme formation, and the dashed residues 52–54 represent a potential N-glycosylation site. The termination TAA codon and the adjacent polyadenylation signal are underlined. Amino acid residues 1–41, 79–95, 111–142, and 162–179 correspond to known tryptic peptide sequences determined by conventional amino acid sequencing analysis.

FIG. 3 is a comparison of N-terminal sequences of *Der p* and *Der f* I. The amino acid sequence for *Der p* I is equivalent to amino acids 1–20 in FIG. 1; the *Der f* I sequence is from reference (12).

FIG. 4 shows the reactivity of λgt11 p1(13T) with anti-*Der p* I. Lysates from Y1089 lysogens induced for phage were reacted by dot-blot with rabbit anti-*Der p* I (*Der p* I) or normal rabbit serum (Nrs). Dots (2 μl) were made in triplicate from lysates of bacteria infected with λgt11 p1(13T) (a) or λgt11 (b). When developed with $^{125}$I-protein A and autoradiography only the reaction between λgt11 p1(13T) lysate and the anti-*Der p* I showed reactivity.

The bacteria were pelleted and resuspended in PBS to 1/10 the volume of culture media. The bacteria were lysed by freeze/thaw and sonication. A radioimmune dot-blot was performed with 2 μl of these lysates using mite-allergic or non-allergic serum. The dots in row 1 were from *E. coli* containing pGEX and row 2–4 from different cultures of *E. coli* infected with pGEX-p1(13T). Reactivity to pGEX-p1 (13T) was found with IgE in allergic but not non-allergic serum. No reactivity to the vector control or with non-allergic serum was found.

Figure 6:
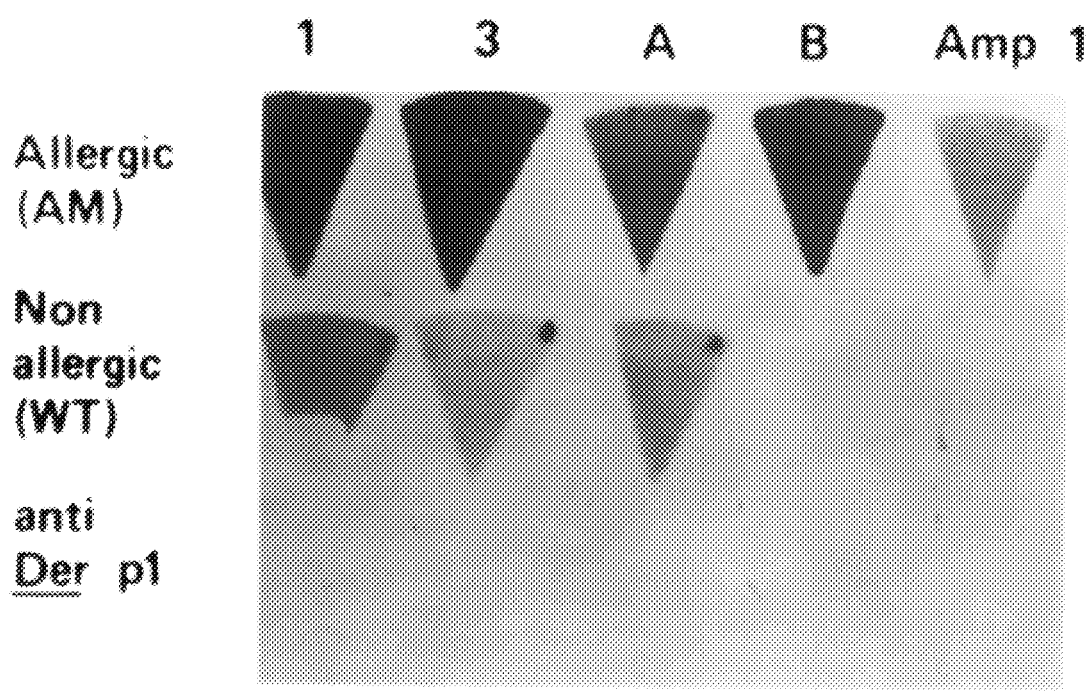

FIG. 6 shows seroreactivity of cDNA clones coding for *Der p* II in plaque radioimmune assay. Segments of nitrocellulose filters from plaque lifts were taken from clones 1, 3, A, B and the vector control Amp1. These were reached by immunoassay for human IgE against allergic serum (AM) in row 1, non-allergic serum (WT) in row 2 and by protein A immunoassay for *Der p* I with rabbit antiserum in row 3. The clones 1, 3 and B reacted strongly with allergic serum but not non-allergic or vector control. (Clone B and vector control were not tested with non-allergic serum).

FIGS. 7A and 7B show the nucleotide and predicted amino acid sequence of cDNA of λgt11 p II (C1). Numbers to the right are nucleotide positions and numbers above are amino acid positions. Positive numbers for amino acids begin at the known N-terminal of *Der p* II and match the known sequence of the first 40 residues. Residues −1 to −16 resemble a typical leader sequence with a hydrophobic core.

FIG. 8 shows the N-terminal amino acid homology of *Der p* II and *Der f* II. (*Der f* II sequence from reference 30).

Figure 9:
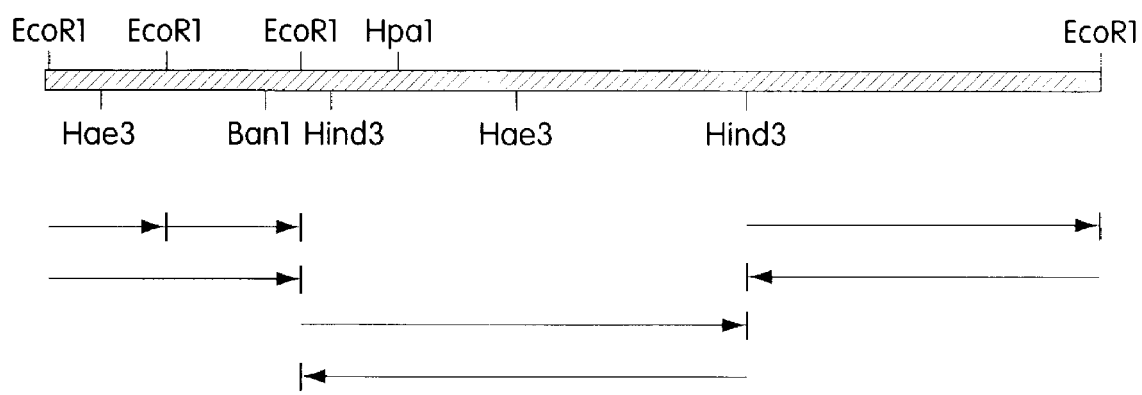

FIG. 9 is a restriction map of the cDNA insert of clone λgt11 f 1, including a schematic representation of the strategy of DNA sequencing. Arrows indicate directions in which sequences were read.

FIGS. 10A and 10B show the nucleotide sequence and the predicted amino acid sequence of cDNA λgt11 f 1. Numbers above are nucleotide positions; numbers to the left are amino acid positions. Positive amino acid residue numbers correspond to the sequence of the mature excreted *Der f* I beginning with threonine. Negative sequence numbers refer to the signal peptide and the proenzyme regions of *Der f* I. The arrows indicate the beginning of the proenzyme sequence and the mature *Der f* I, respectively. The underlined residues −81 to −78 make up the proposed cleavage site for the proenzyme formation, while the underlined residues 53–55 represent a potential N-glycosylation site. The termination TGA codon and the adjacent polyadenylation signal are also underlined. Amino acid residues 1–28 correspond to a known tryptic peptide sequence determined by conventional amino acid sequencing analysis.

FIG. 11 is a composite alignment of the amino acid sequences of the mature *Der p* I and *Der f* I proteins. The numbering above the sequence refers to *Der p* I. The asterisk denotes the gap that was introduced for maximal alignment. The symbol (.) is used to indicate that the amino acid residue of *Der f* I at that position is identical to the corresponding amino acid residue of *Der p* I. The arrows indicate those residues making up the active site of *Der p* I and *Der f* I.

FIGS. 12A and 12B show is a comparison of the amino acid sequence in the pre- and pro-peptide regions of *Der f* I with those of rat cathepsin H. rat cathepsin L, papain, aleurain, CP1, CP2, rat cathepsin B, CTLA-2, MCP, *Der p* I and actinidin. Gaps, denoted by dashes, were added for maximal alignment. Double asterisks denote conserved amino acid residues which are shared by greater than 80% of the proenzymes; single asterisks show residues which are conserved in greater than 55% of the sequences. The symbol (.) is used to denote semiconserved equivalent amino acids which are shared by greater than 90% of the proenzyme regions.

Figure 13A:
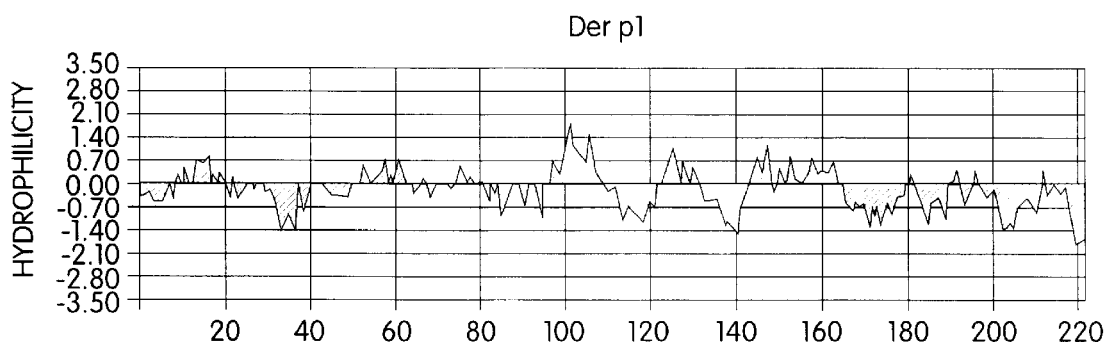
Figure 13B:
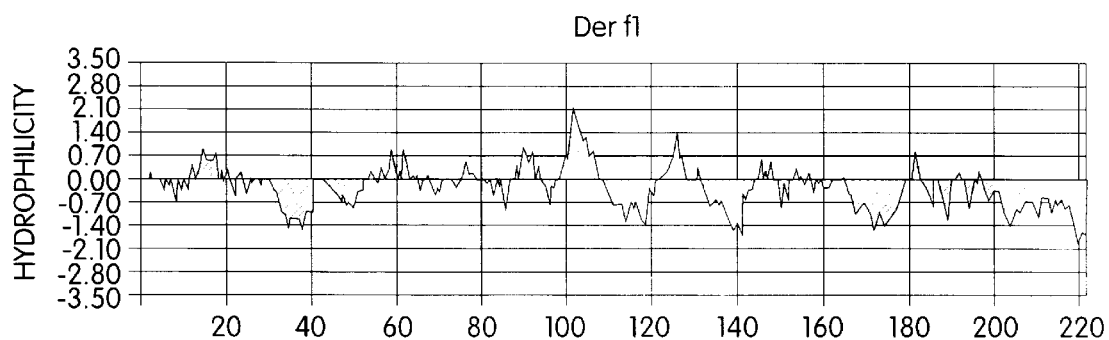

FIGS. 13A and 13B show is a hydrophilicity plot of the *Der p* I mature protein and a hydrophilicity plot of the *Der f* I mature protein produced using the Hopp-Woods algorithm computed with the Mac Vector Sequence Analysis Software (IBI, New Haven) using a 6 residue window. Positive values indicate relative hydrophilicity and negative values indicating relative hydrophobicity.

FIG. 14 is the nucleotide sequence and the predicted amino acid sequence of *Der f* II cDNA. Numbers to the right are nucleotide positions and numbers above are amino acid residues. The stop (TAA) signal is underlined. The first 8 nucleotides are from the oligonucleotide primer used to generate the cDNA, based on the *Der p* II sequence.

Figure 15:
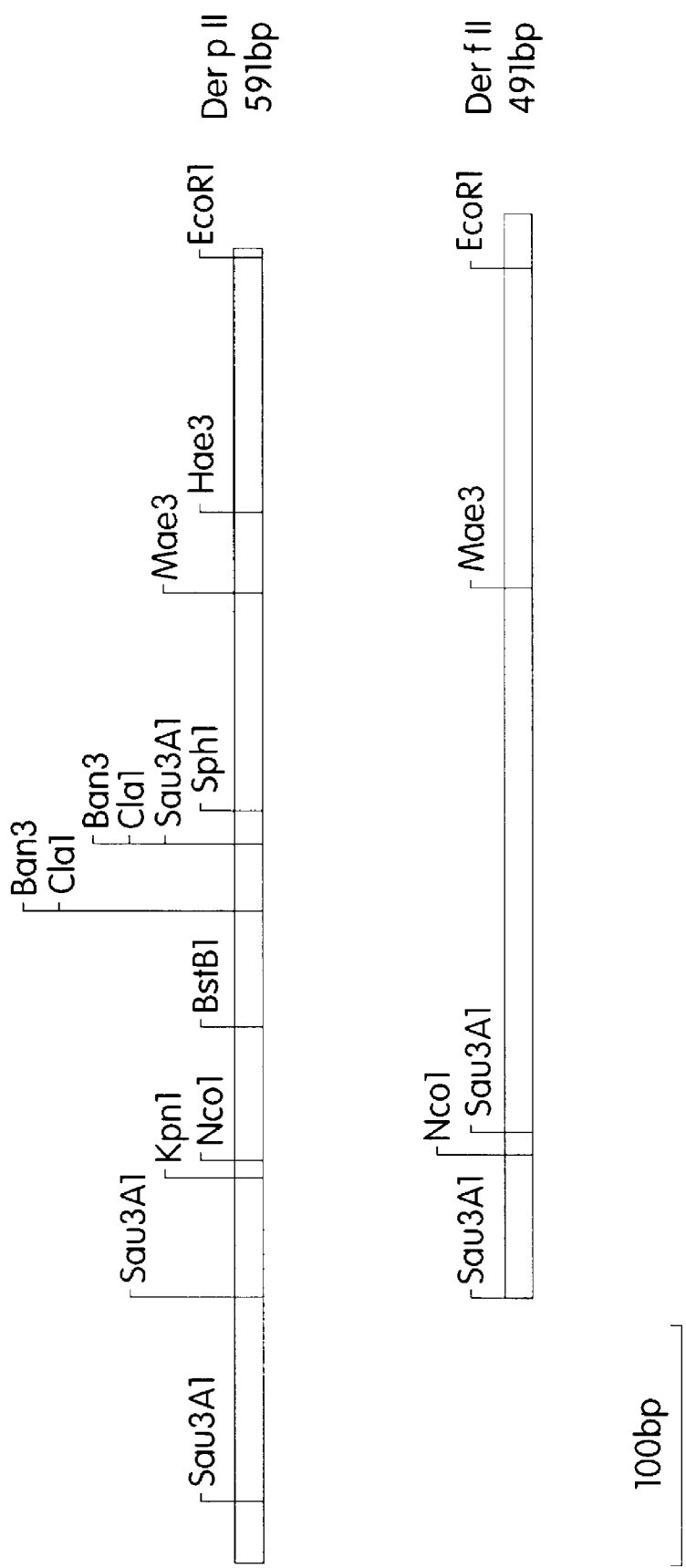

FIG. 15 is a restriction map of *Der f* II cDNA, which was generated by computer from the sequence data. A map of *Der p* II similarly generated is shown for comparison. There are few common restriction enzyme sites conserved. Sites marked with an asterisk were introduced by cloning procedures.

FIGS. 16A, 16B and 16C show the alignment of *Der f* II and *Der p* II cDNA sequences. Numbers to the right are nucleotide position and numbers above are amino acid residues. The top line gives *Der p* II nucleotide sequence and the second the *Der p* II amino acid residues. The next two lines show differences of *Der f* II to these sequences.

Figure 17A:
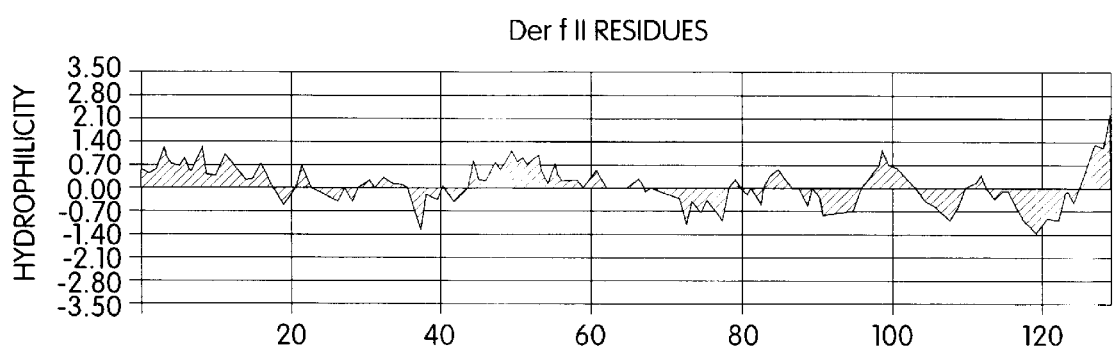
Figure 17B:
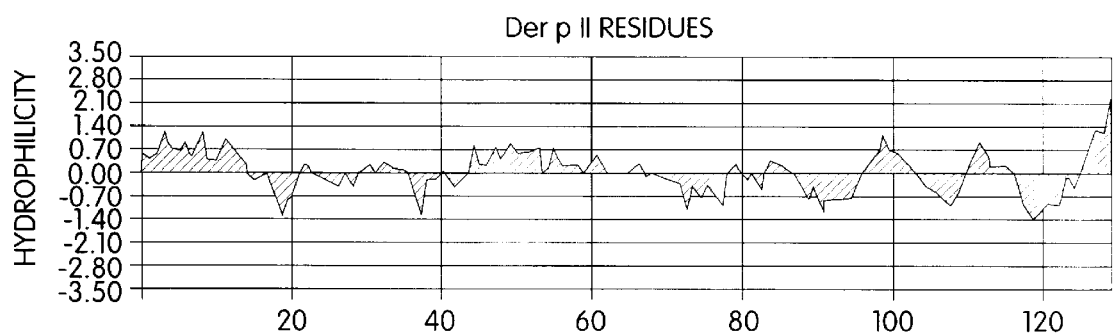

FIG. 17A and 17B show is a hydrophilicity plot of *Der f* II and *Der p* II using the Hopp-Woods algorithm computed with the Mac Vector Sequence Analysis Software (IBI, New Haven) using a 6-residue window.

FIG. 18 is a composite alignment of the amino acid sequences of five *Der p* I clones (a)–(e) which illustrates polymorphism in the *Der p* I protein. The numbering refers to the sequence of the *Der p* I(a) clone. The symbol (−) is used to indicate that the amino acid residue of a *Der p* I clone is identical to the corresponding amino acid residue of *Der p* I(a) at that position. The amino acid sequences of these clones indicate that there may be significant variation in *Der p* I, with five polymorphic amino acid residues found in the five sequences.

FIG. 19 is a composite alignment of the amino acid sequences of three *Der p* II clones (c), (1) and (2) which illustrates polymorphism in the *Der p* II protein. The numbering refers to the sequence of the *Der p* II(c) clone. The symbol (.) is used to indicate that the amino acid residue of a *Der p* II clone is identical to the corresponding amino acid residue of *Der p* II (c) at that position.

FIG. 20 is a composite alignment of the amino acid sequences of six *Der f* II clones (i.e., pFL1, pFL2, MT3, MT5, MT18 and MT16) which illustrates polymorphism in the *Der f* II protein. The numbering refers to the sequences of the *Der f* pFL1 clone. The symbol (.) is used to indicate that the amino acid residue of a *Der f* II clone is identical to the corresponding amino acid residue of *Der f* II pFL1 at that position.

FIG. 21A, 21B and 21C show the nucleotide and predicted amino acid sequences of cDNA λgt11 p1(13T), including the full length of the preproenzyme form of *Der p* I. Negative sequence numbers refer to the proposed pre- and preproenzyme forms of *Der p* I.

DETAILED DESCRIPTION OF THE INVENTION

The present invention relates to a nucleotide sequence coding for an allergen from the house dust mite Dermatophagoides and to the encoded Dermatophagoides protein or peptide which includes at least one epitope of the Dermatophagoides allergen. It particularly relates to a nucleotide sequence capable of expression in an appropriate host of a major allergen of D. farinae, such as Der f I or Der f II, or of a peptide which includes at least one epitope of Der f I or of Der f II. It also particularly relates to a nucleotide sequence capable of expression in an appropriate host of a major allergen of D. pteronyssinus, such as Der p I or Der p II, or of a peptide which includes at least one epitope of Der p I or of Der p II. The Dermatophagoides nucleotide sequence is useful as a probe for identifying additional nucleotide sequences which hybridize to it and encode other mite allergens, particularly D. farinae or D. pteronyssinus allergens. Further, the present invention relates to nucleotide sequences which hybridize to a D. farinae protein-encoding nucleotide sequence or a D. pteronyssinus protein-encoding nucleotide sequence but which encode a protein from another species or type of house dust mite, such as D. microceras (e.g., Der m I and Der m II).

The encoded Dermatophagoides mite allergen or peptide which includes at least one Dermatophagoides (Der f I or Der f II; Der p I or Der p II) epitope can be used for diagnostic purposes (e.g., as an antigen) and for therapeutic purposes (e.g., to desensitize an individual). Alternatively, the encoded house dust mite allergen can be a protein or peptide, such as a D. microceras protein or peptide, which displays the antigenicity of or is cross-reactive with a Der f or a Der p allergen; generally, these have a high degree of amino acid homology.

Accordingly, the present invention also relates to compositions which include a Dermatophagoides allergen (e.g., Der f I allergen, Der f II allergen; Der p I or Der p II allergen or other D allergen cross-reactive therewith),or a peptide which includes at least one epitope of a Dermatophagoides allergen (Der f I, Der f II, Der p I, Der p II or other D. allergen cross-reactive therewith) individually or in combination, and which can be used for therapeutic applications (e.g., desensitization). As is described below, DNA coding for major allergens from house dust mites have been isolated and sequenced. In particular, and as is described in greater detail in the Examples, cDNA clones coding for the Der p I, Der p II, Der f I and Der f II allergens have been isolated and sequenced. The nucleotide sequence of each of these clones has been compared with that of the homologous allergen from the related mite species (i.e., Der p I and Der f I; Der p II and Der f II), as has the predicted amino acid sequence of each.

The following is a description of isolation and sequencing of the two cDNA clones coding for Der f allergens and their comparison with the corresponding D. pteronyssinus allergen and a description of use of the nucleotide sequences and encoded products in a diagnostic or a therapeutic context.
Isolation and Sequence Analysis of Der f I A cDNA clone coding for Der f I, a major allergen from the house dust mite D. farinae, has been isolated and sequenced. A restriction map of the cDNA insert of the clone is represented in FIG. 9, as is the strategy of DNA sequencing. This Der f I cDNA clone contains a 1.1-kb cDNA insert encoding a typical signal peptide, a proenzyme region and the mature Der f I protein. The product is 321 amino acid residues; a putative 18 residue signal peptide, an 80 residue proenzyme (pro-peptide) region, and a 223 residue mature enzyme region. The derived molecular weight is 25,191. The nucleotide sequence and the predicted amino acid sequence of the Der f I cDNA are represented in FIG. 10. The deduced amino acid sequence shows significant homology to other cysteine proteases in the pro-region, as well as in the mature protein. Sequence alignment of the mature Der f I protein with the homologous allergen Der p I from the related mite D. pteronyssinus (FIG. 11) revealed a high degree of homology (81%) between the two proteins, as predicted by previous sequencing at the protein level. In particular, the residues comprising the active site of these enzymes were conserved and a potential N-glycosylation site was present at equivalent positions in both mite allergens.

Conserved cysteine residue pairs (31, 71) and (65, 103), where the numbering refers to Der p I, are apparently involved in disulphide bond formation on the basis of the assumed similarity of the three dimensional structure of Der p I and Der f I to that of papain and actinidin, which also have an additional disulphide bridge. The fifth and final cysteine residue for which there is a homologous cysteine residue in papain-and actinidin is the active site cysteine (residue 35 in Der f I). It is not unlikely that the two extra cysteine residues present in Der p I and Der f I may be involved in forming a third disulphide bridge.

The potential N-glycosylation site in Der p I is also present at the equivalent position in Der f I, with conservation of the crucial first and last residues of the tripeptide site. The degree of glycosylation of Der f I and Der p I has yet to be determined. Carbohydrates, including mannose, galactose, N-acetylglucosamine and N-acetylgalactosamine, have been reported in purified preparations of these mite allergens (Chapman, M. D., J. Immunol., 12:587–592 (1980); Wolden, S. et al., Int. Arch. Allergy Appl. Immunol., 68:144–151 (1982)).

Given the degree of homology over the first thirty N-terminal amino acid residues between mature Der p I and Der m I (70%) and mature Der f I and Der m I (97%) with the Der m I residues determined by conventional amino acid sequencing (Platts-Mills TAE et al., In: Mite Allergy, a World-Wide Problem, 27–29 (1988); Lind, P. and N. Horn, In: Mite Allergy, a World-Wide Problem, 30–34 (1988)), it is probable that the full mature Der m I sequence will confirm an overall 70–80% homology between the Group I mite allergens. Der m I is an allergen from D. microceras. High homology between the proenzyme moieties of Der p I and Der f I (91%) over the residues −23 to −1 and the structural analysis of Der f I suggests that the Group I allergens are likely to have N-terminal extension peptides of the mature protein of homologous structure and, at least for the pro-peptide, composition.

Studies on the fine structure of the design of signal sequences have identified three structurally dissimilar regions so far: a positively charged N-terminal (n) region, a central hydrophobic (h) region and a more polar C-terminal (c) region that seems to define the cleavage site (Von Heijne, G., EMBO J., 3:2315–2323 (1984); Eur. J. Biochem., 133:1714 21 (1983); J. Mol. Biol., 184:99–105 (1985)). Analysis of the signal peptide of Der f I revealed that it, too, contained these regions (FIG. 12). The n-region is extremely variable in length and composition, but its net charge does not vary appreciably with the overall length, and has a mean value of about +1.7. The n-region of the Der f I signal peptide, with a length of two residues, has a net charge of +2 contributed by the initiator methionine (which is unformylated and hence positively charged in eukaryotes) and the adjacent lysine (Lys) residue. The h-region of Der f I is enriched with hydrophobic residues, the characteristic feature of this region, with only one hydrophilic residue serine (Ser) present which can be tolerated. The overall amino acid composition of the Der f I c-region is more polar than that of the h-region as is found in signal sequences with the h/c boundary located between residues −6 and −5, which is its mean position in eukaryotes. Thus, the *Der f* I pre-peptide sequence appears to fulfill the requirements to which a functional signal sequence must conform.

While the signal sequence of *Der f* I and other cysteine proteases share structural homology, all being composed of the n,h and c-regions, they are highly variable with respect to overall length and amino acid sequence, as is clear in FIG. 12. However, significant sequence homology has been shown between the pro-regions of cysteine protease precursors (Ishidoh, K. et al., *FEBS Letters*, 226:33–37 (1987)). Alignment of the proenzyme regions of *Der f* I and a number of other cysteine proteases (FIG. 12) indicated that these proregions share a number of very conserved residues as well as semi-conserved residues which were present in over half of the sequences. This homology was increased if conservative amino acids such as valine (Val), isoleucine (Ile) and leucine (Leu) (small hydrophobic residues) or arginine (Arg) and Lys (positively charged residues) were regarded as identical. The *Der f* I proregion possessed six out of seven highly conserved amino acids and all the residues at sites of conservative changes. The homology at less conserved sites was lower. Homology in the pro-peptide, in particular the highly conserved residues, may be important when considering the function of the pro-peptide in the processing of these enzymes, since it indicates that these sequences probably have structural and functional similarities.

Highly cross-reactive B cell epitopes on *Der f* I and *Der p* I have been demonstrated using antibodies present in mouse, rabbit and human sera (Heymann, P. W. et al., *J. Immunol.* 137:2841–2847 (1986); Platts-Mills, TAE et al., *J. Allergy Clin. Immunol.* 78:398–407 (1986)). However, species-specific epitopes have also been defined in these systems. Murine monoclonal antibodies bound predominantly to species-specific determinants (Platts-Mills TAE et al., *J. Allergy Clin. Immunol.* 139:1479–1484 (1987)). Some 40% of rabbit anti-*Der p* I reactivity was accounted for by epitopes unique to *Der p* I (Platts-Mills, TAE et al., *J. Allergy Clin. Immunol.* 78:398–407 (1986)), and some species-specific binding of antibodies from allergic humans was observed, although the majority bind to cross-reactive epitopes (Platts-Mills TAE et al., *J Immunol.* 139:1479–1484 (1987)).

The recombinant DNA strategy of gene fragmentation and expression was used (Greene, W. K. et al., *Immunol.* (1990)) to define five antigenic regions of recombinant *Der p* I which contained B cell epitopes recognized by a rabbit anti-*Der p* I antiserum. Using the technique of immunoabsorption, three of these putative epitopes were shown to be shared with *Der f* I (located on regions containing amino acid residues 34–47, 60–72 and 166–194) while two appeared to be specific for *Der p* I (regions 82–99 and 112–140). Differences in the reactivity of these peptides to rabbit anti-*D. farinae* supported the above division into cross-reactive and species-specific epitopes. The sequence differences shown between the *Der p* I and the *Der f* I proteins are primarily located in the N and C terminal regions, as well as in an extended surface loop (residues 85–136) linking the two domains of the enzyme that includes helix D (residues 127–136), as predicted from the secondary and tertiary structures of papain and actinidin (Baker, E. N. and J. Drenth, In: *Biological Macromolecules and Assemblies*, Vol. 3, pp. 314–368, John Wiley and Sons, NY (1987)). The surface location of these residues is supported by the hydrophilicity plots of *Der p* I and *Der f* I in FIG. 13, which illustrate the predominantly hydrophilic nature of this region that predicts surface exposure. This region also contains the two species-specific B cell epitopes recognized by the rabbit anti-*Der p* I serum (see above). Analysis of the sequences in the regions containing the cross-reactive epitopes (located in regions 34–47 and 60–72) are completely conserved between *Der p* I and *Der f* I, while the majority of residues in a third cross-reactive epitope-containing region (residues region 166–194) were conserved.

Expression of cDNA encoding *Der f* I results in production of pre-pro-*Der f* I protein in *E. coli*, a recombinant protein of greater solubility, stability and antigenicity than that of recombinant *Der p* I. Protein encoded by *Der f* I cDNA has been expressed using a pGEX vector and has been shown by radioimmune assay to react with rabbit anti-*D. farinae* antibodies. The availability of high yields of soluble *Der f* I allergen and antigenic derivatives will facilitate the development of diagnostic and therapeutic agents and the mapping of B and T cell antigenic determinants.

With the availability of the complete amino acid sequence of recombinant *Der f* I, mapping of the epitopes recognized by both the B and T cell compartments of the immune system can be carried out. The use of techniques such as the screening of overlapping synthetic peptides, the use of monoclonal antibodies and gene fragmentation and expression should enable the identification of both the continuous and topographical epitopes of *Der f* I. It will be particularly useful to determine whether allergenic (IgE-binding) determinants have common features and are intrinsically different from antigenic (IgG-binding) determinants and whether T cells recognize unique epitopes different from those recognized by B cells. Studies to identify the *Der f* I epitopes reactive with mite allergic human IgE antibodies and the division of these into determinants cross-reactive with *Der p* I and determinants unique to *Der f* I can also be carried out. B cell (and T cell) epitopes specific for either species can be used to provide useful diagnostic reagents for determining reactivity to the different mite species, while cross-reacting epitopes are candidates for a common immunotherapeutic agent.

As described in detail in the Examples, a cDNA clone coding for *Der p* I which contained a 0.8-kb cDNA insert has been isolated. Sequence analysis revealed that the 222 amino acid residue mature recombinant *Der p* I protein showed significant homology with a group of cysteine proteases, including actinidin, papain, cathepsin H and cathepsin B.

Isolation and Sequence Analysis of *Der f* II

A cDNA clone coding for *Der f* II, a major allergen from the house dust mite *D. farinae*, has been isolated and sequenced, as described in the Examples. The nucleotide sequence and the predicted amino acid sequence of the *Der f* II cDNA are represented in FIG. 14. A restriction map of the cDNA insert of a clone coding for *Der f* II is represented in FIG. 15.

FIG. 16 shows the alignment of *Der f* II and *Der p* II cDNA sequences. The homology of the sequence of *Der f* II with *Der p* II (88%) is higher than the 81% homology found with *Der p* I and *Der f* I, which is significantly different ($p<0.05$) using the $chi^2$ distribution. The reason for this may simply be that the Group I allergens are larger and each residue may be less critical for the structure and function of the molecule. It is known, for example, that assuming they adopt a similar conformation to other cysteine proteases, many of the amino acid differences in *Der p* I and *Der f* I lie in residues linking the two domain structures of the molecules. The 6 cysteine molecules are conserved between the group II allergens, suggesting a similar disulphide bonding, although this may be expected, given the high overall homology. Another indication of the conservation of these proteins is that 34/55 of the nucleotide changes of the coding sequence are in the third base of a codon, which usually does not change the amino acid. Residues that may be of importance in the function of the molecule are Ser 57 where all three bases are changed but the amino acid is conserved. A similar phenomenon exists at residue 88, where a complete codon change has conserved a small aliphatic residue. Again, like Der p II, the Der f II cDNA clone does not have a poly A tail, although the 3' non-coding region is rich in adenosine and has two possible polyadenylation signals ATAA. The nucleotides encoding the first four residues are from the PCR primer which was designed from the known homology of Der p II and Der f II from N-terminal amino acid sequencing. A primer based on the C-terminal sequence can now be used to determine these bases, as well as the signal sequence.

Uses of the subject allergenic proteins/peptides and DNA encoding same

The materials resulting from the work described herein, as well as compositions containing these materials, can be used in methods of diagnosing, treating and preventing allergic responses to mite allergens, particularly to mites of the genus Dermatophagoides, such as D. farinae and D pteronyssinus. In addition, the cDNA (or the mRNA from which it was transcribed) can be used to identify other similar sequences. This can be carried out, for example, under conditions of low stringency and those sequences having sufficient homology (generally greater than 40%) can be selected for further assessment using the method described herein. Alternatively, high stringency conditions can be used. In this manner, DNA of the present invention can be used to identify sequences coding for mite allergens having amino acid sequences similar to that of Der f I, Der f II, Der p I or Der p II. Thus, the present invention includes not only D. farinae and D. pteronyssinus allergens, but other mite allergens as well (e.g., other mite allergens encoded by DNA which hybridizes to DNA of the present invention).

Proteins or peptides encoded by the cDNA of the present invention can be used, for example, as "purified" allergens. Such purified allergens are useful in the standardization of allergen extracts or preparations which can be used as reagents for the diagnosis and treatment of allergy to house dust mites. Through use of the peptides of the present invention, allergen preparations of consistent, well-defined composition and biological activity can be made and administered for therapeutic purposes (e.g., to modify the allergic response of a house dust mite-sensitive individual). Der f I or Der f II peptides or proteins (or modified versions thereof, such as are described below) may, for example, modify B-cell response to Der f I or Der f II, T-cell response to Der f I and Der f II, or both responses. Similarly, Der p I or Der p II proteins or peptides may be used to modify B-cell and/or T-cell response to Der p I or Der p II. Purified allergens can also be used to study the mechanism of immunotherapy of allergy to house dust mites, particularly to Der f I, Der f II, Der p I and Der p II, and to design modified derivatives or analogues which are more useful in immunotherapy than are the unmodified ("naturally-occurring") peptides.

In those instances in which there are epitopes which are cross-reactive, such as the three epitopes described herein which are shared by Der f I and Der p I, the area(s) of the molecule which contain the cross-reactive epitopes can be used as common immunotherapeutic peptides to be administered in treating allergy to the two (or more) mite species which share the epitope. For example, the cross-reactive epitopes could be used to induce IgG blocking antibody against both allergens (e.g., Der f I and Der p I allergen). A peptide containing a univalent antibody epitope can be used, rather than the entire molecule, and may prove advantageous because the univalent antibody epitope cannot crosslink mast cells and cause adverse reactions during desensitizing treatments. It is also possible to attach a B cell epitope to a carrier molecule to direct T cell control of allergic responses.

Alternatively, it may be desirable or necessary to have peptides which are specific to a selected Dermatophagoides allergen. As described herein, two epitopes which are apparently Der p I-specific have been identified. A similar approach can be used to identify other species-specific epitopes (e.g., Der p I or II, Der f I or II). The presence in an individual of antibodies to the species-specific epitopes can be used as a quick serological test to determine which mite species is causing the allergic response. This would make it possible to specifically target therapy provided to an individual to the causative species and, thus, enhance the therapeutic effect.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a peptide of the present invention (e.g., one having all or a portion of the amino acid sequence of Der f I or Der f II, Der p I or Der p II). Alternatively, a combination of peptides can be administered. A modified peptide or peptide analogue (e.g., a peptide in which the amino acid sequence has been altered to modify immunogenicity and/or reduce allergenicity or to which a component has been added for the same purpose) can be used for desensitization therapy.

Administration of the peptides of the present invention to an individual to be desensitized can be carried out using known techniques. A peptide or combination of different peptides can be administered to an individual in a composition which includes, for example, an appropriate buffer, a carrier and/or an adjuvant. Such compositions will generally be administered by injection, inhalation, transdermal application or rectal administration. Using the information now available, it is possible to design a Der p I, Der p II, Der f I or Der f II peptide which, when administered to a sensitive individual in sufficient quantities, will modify the individual's allergic response to Der p I, Der p II, Der f I and/or Der f II. This can be done, for example, by examining the structures of these allergens, producing peptides to be examined for their ability to influence B-cell and/or T-cell responses in house dust mite-sensitive individuals and selecting appropriate epitopes recognized by the cells. Synthetic amino acid sequences which mimic those of the epitopes and which are capable of down regulating allergic response to Der p I, Der p II, Der f I or Der f II allergens can be made. Proteins, peptides or antibodies of the present invention can also be used, in known methods, for detecting and diagnosing allergic response to Der f I or Der f II. For example, this can be done by combining blood obtained from an individual to be assessed for sensitivity to one of these allergens with an isolated allergenic peptide of house dust mite, under conditions appropriate for binding of or stimulating components (e.g., antibodies, T cells, B cells) in the blood with the peptide and determining the extent to which such binding occurs. Der f and Der p proteins or peptides can be administered together to treat an individual sensitive to both allergen types.

It is now also possible to design an agent or a drug capable of blocking or inhibiting the ability of Der p I, Der p II, Der f I or Der f II to induce an allergic reaction in house dust mite-sensitive individuals. Such agents could be designed, for example, in such a manner that they would bind to relevant anti-Der p I, anti-Der p II, anti-Der f I or anti-Der f II IgEs, thus preventing IgE-allergen binding and subsequent mast cell degranulation. Alternatively, such agents could bind to cellular components of the immune system, resulting in suppression or desensitization of the allergic response to these allergens. A non-restrictive example of this is the use of appropriate B- and T-cell epitope peptides, or modifications thereof, based on the cDNA/protein structures of the present invention to suppress the allergic response to these allergens. This can be carried out by defining the structures of B- and T-cell epitope peptides which affect B- and T-cell function in in vitro studies with blood cells from house dust mite-sensitive individuals.

The cDNA encoding Der p I, Der p II, Der f I or Der f II or a peptide including at least one epitope thereof can be used to produce additional peptides, using known techniques such as gene cloning. A method of producing a protein or a peptide of the present invention can include, for example, culturing a host cell containing an expression vector which, in turn, contains DNA encoding all or a portion of a selected allergenic protein or peptide (e.g., Der p I, Der p II, Der f I, Der f II or a peptide including at least one epitope). Cells are cultured under conditions appropriate for expression of the DNA insert (production of the encoded protein or peptide). The expressed product is then recovered, using known techniques. Alternatively, the allergen or portion thereof can be synthesized using known mechanical or chemical techniques. As used herein, the term protein or peptide refers to proteins or peptides made by any of these techniques. The resulting peptide can, in turn, be used as described previously.

DNA to be used in any embodiment of this invention can be cDNA obtained as described herein or, alternatively, can be any oligodeoxynucleotide sequence having all or a portion of the sequence represented in FIGS. 1, 7, 10 and 14 or their functional equivalent. Such oligodeoxynucleotide sequences can be produced chemically or mechanically, using known techniques. A functional equivalent of an oligonucleotide sequence is one which is capable of hybridizing to a complementary oligonucleotide sequence to which the sequence (or corresponding sequence portions) of FIGS. 1, 7, 10 and 14 hybridizes and/or which encodes a product (e.g., a polypeptide or peptide) having the same functional characteristics of the product encoded by the sequence (or corresponding sequence portion) represented in these figures. Whether a functional equivalent must meet one or both criteria will depend on its use (e.g., if it is to be used only as an oligoprobe, it need meet only the first criterion and if it is to be used to produce house dust mite allergen, it need only meet the second criterion).

The structural information now available (e.g., DNA, protein/peptide sequences) can also be used to identify or define T cell epitope peptides and/or B cell epitope peptides which are of importance in allergic reactions to house dust mite allergens and to elucidate the mediators or mechanisms (e.g., interleukin-2, interleukin-4, gamma interferon) by which these reactions occur. This knowledge should make it possible to design peptide-based house dust mite therapeutic agents or drugs which can be used to modulate these responses.

The present invention will now be further illustrated by the following Examples, which are not intended to be limiting in any way.

EXAMPLE 1

MATERIALS AND METHODS

Cloning and Expression of Der p I cDNA

Polyadenylated mRNA was isolated from the mite Dermatophagoides pteronyssinus cultured by Commonwealth Serum Laboratories, Parkville, Australia, and cDNA was synthesized by the RNA-ase H method (5) using a kit (Amersham, International, Bucks). After the addition of EcoRI linkers the cDNA was ligated into λgt11 and plated in E coli Y1090 (r-) (Promega Biotec, Madison, Wis.), to produce a library of $5 \times 10^5$ recombinants. Screening was performed by plaque radioimmune assay (6) using a rabbit anti-Der p I antiserum (7). Reactivity was detected by hydrochloride in 0.1M sodium acetate buffer pH 5.2 were then added and the mixture was homogenized and spun at 10,000 rpm for 30 min in a Sorval SS34 rotor. The supernatant was collected and layered onto a CsCl pad (5 ml of 4.8M CsCl in 10 mM EDTA) and centrifuged at 37,000 rpm for 16 h at 15° C. in a SW41 TI rotor (Beckman Instruments, Inc., Fullerton, Calif.). The DNA band at the interphase was collected and diluted 1:15 in 10 mM Tris HCl/1 mM EDTA buffer, pH 8.0. Banding of genomic DNA in CsCl was carried out by the standard method.

Isolation of DNA from λgt11 p1 cDNA Clone

Phage DNA from λgt11 p1 clone was prepared by a rapid isolation procedure. Clarified phage plate lysate (1 ml) was mixed with 270 µl of 25% wt/vol polyethylene glycol (PEG 6000) in 2.5M NaCl and incubated at room temperature for 15 min. The mixture was then spun for 5 min in a microfuge (Eppendorf, Federal Republic of Germany), and the supernatant was removed. The pellet was dissolved in 100 µl of 10 mM Tris/HCl pH 8.0 containing 1 mM EDTA and 100 mM NaCl. This DNA preparation was extracted 3 times with phenol/chloroform (1:1) and the DNA was precipitated by ethanol.

DNA Hybridization

Nucleic acid was radiolabelled with $^{32}P$ by nick translation (10). DNA samples were digested with appropriate restriction enzymes using conditions recommended by the supplier. Southern blots were prepared using Zeta-Probe membranes (Bio-Rad Laboratories, Richmond, Calif.). Prehybridization, hybridization, posthybridization washes were carried out according to the manufacturers recommendations (bulletin 1234, Bio-Rad Laboratories).

Cloning and DNA Sequencing

To clone the 0.8-kb cDNA insert from clone λgt11 p1 into plasmid pUC8, phage DNA was digested with EcoRI restriction enzyme and then ligated to EcoRI-digested pUC8 DNA and used to transform Escherichia coli JM83. The resulting recombinant plasmid was designated as pHDM 1.

To obtain clones for DNA sequence analysis, the cDNA insert was isolated from pHDM 1 and ligated to M13-derived sequencing vectors mp18 and mp19 (16). Transformation was carried out using E. coli JM107 and sequencing was performed by the dideoxynucleotide chain termination method (11).

RESULTS

Figure 2:
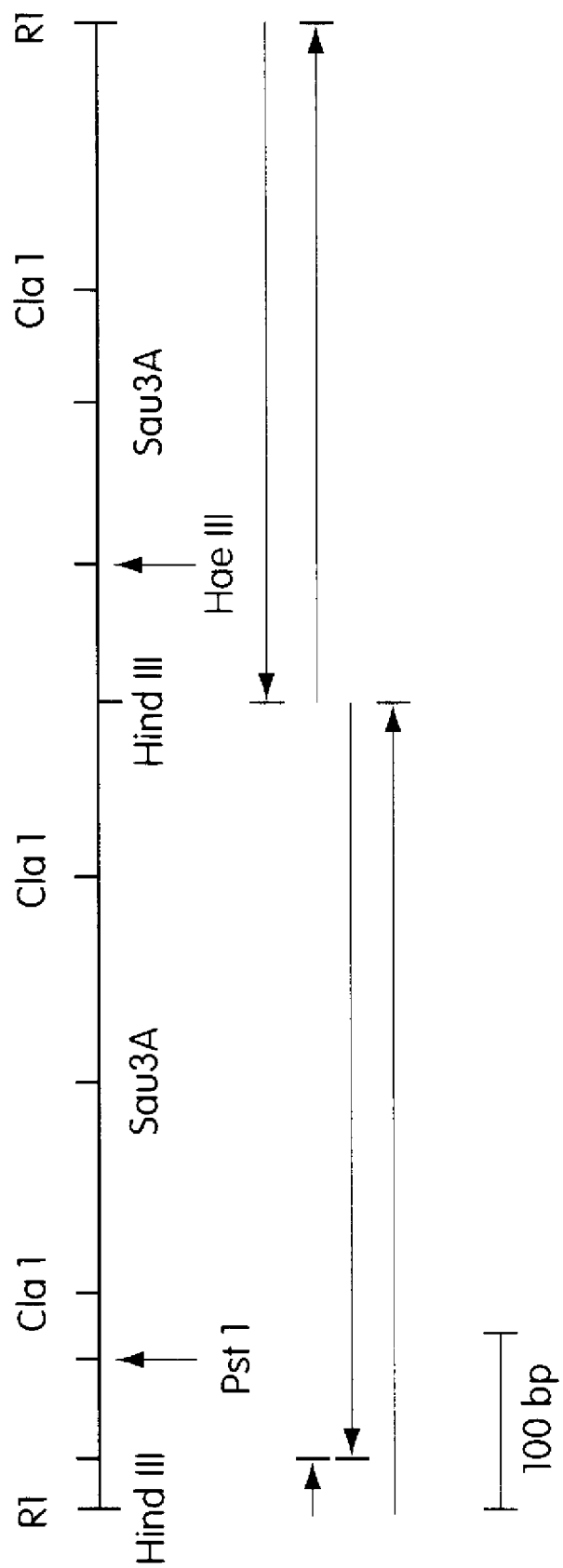
FIG. 2 shows the restriction map of the cDNA insert of clone λgt11 p1 (13T) and the strategy of DNA sequencing. Arrows indicate directions in which sequences were read.

Several phage clones reacted with the rabbit anti Der p I serum and hybridized with all 3 oligonucleotide probes. One of these, λgt11 p1(13T), was examined further. The nucleotide sequence of the cDNA insert from this clone, λgt11 p1, was determined using the sequencing strategy shown in FIG. 2. The complete sequence was shown to be 857 bases long and included a 69-base-long 5' proximal end sequence, a coding region for the entire native Der p I protein of 222 amino acids with a derived molecular weight of 25,371, an 89-base-long 3' noncoding region and a poly (A) tail of 33 residues (FIG. 1).

The assignment of a threonine residue at position 1 as the $NH_2$-terminal amino acid of Der p I was based on data obtained by $NH_2$-terminal amino acid sequencing of the pure protein isolated from mite excretions (17). The predicted amino acid sequence matched with data obtained by amino acid sequence analysis of the $NH_2$-terminal region as well as with internal sequences derived from analyses of tryptic peptides (FIG. 1). The complete mature protein is coded by a single open reading frame terminating at the TAA stop codon at nucleotide position 736-738. At present, it is not certain whether the first ATG codon at nucleotide position 16-18 is the translation initiation site, since the immediate flanking sequence of this ATG codon (TTGATGA) showed no homology with the Kozak consenses sequence (ACCATGG) for the eukaryotic translation initiation sites (18). In addition, the 5' proximal end sequence does not code for a typical signal peptide sequence (see below).

The amino acid sequence predicted by nucleotide analysis is shown in FIG. 1. A protein data-base search revealed that the Der p I amino acid sequence showed homology with a group of cysteine proteases. Previous cDNA studies have shown that lysosomal cathepsins B, a mouse macrophage protease and a cysteine protease from an amoeba have transient pre- and proform intermediates (19–21), and inspection of the amino acid sequence at the 5' proximal end of the λgt11 p1 cDNA clone suggests that Der p I may be similar. First, the hydrophilicity plot (22) of the sequence preceding the mature protein sequence lacks the characteristic hydrophobic region of a signal peptide (23) and second, an Ala-X-Ala sequence, the most frequent sequence preceding the signal peptidase cleavage site (24,25), is present at positions −13, −14, −15 (FIG. 1). Therefore, it is proposed that cleavage between pro-Der p I sequence and the pre-Der p I sequence occurs between Ala (−13) and Phe (−12). Thus, pro-Der p I sequence begins at residues Phe (−12) and ends at residues Glu (−1). The amino acids residues numbered −13 to −23 would then correspond to a partial signal peptide sequence. The full length of the Der p I preproenzyme sequence has been determined and is shown in FIG. 21. The negative sequence numbers refer to the pre- and preproenzyme forms of Der p I.

When the 857-bp cDNA insert was radiolabelled and hybridized against a Southern blot of EcoRI-digested genomic DNA from house dust mite, hybridization to bands of 1.5, 0.5, and 0.35 kb was observed (data not shown). As shown in the restriction enzyme map of the cDNA insert (FIG. 2), there was no internal EcoRI site and the multiple hybridization bands observed suggest that Der p I is coded by a noncontiguous gene. The results also showed little evidence of gene duplication since hybridization was restricted to fragments with a total length of 2.4 kb.

The N-terminal can be compared with N-terminal of the equivalent protein from D. farinae (Der f I) (12). There is identity in 11/20 positions of the sequences available for comparison (FIG. 3).

To examine the protein produced by λgt11 p1(13T), phage was lysogenized in Y1089 (r−) and the bacteria grown in broth culture at 30° C. Phage was induced by temperature switch and isopropyl thiogalactopyranoside (IPTG) (6) and the bacteria were suspended in PBS to 1/20 of the culture volume, and sonicated for an antigen preparation. When examined by 7.5% SDS-PAGE electrophoresis it was found that λgt11 p1(13T) did not produce a Mr 116K β-galactosidase band but instead produced a 140K band consistent with a fusion protein with the Der p I contributing a 24 kDa moiety (6). Rabbit anti Der p I was shown to react with the lysate from λgt11 p1(13T) (FIG. 4).

EXAMPLE 2

Expression of Der p I cDNA products reactive with IgE from allergic serum.

Figure 5:
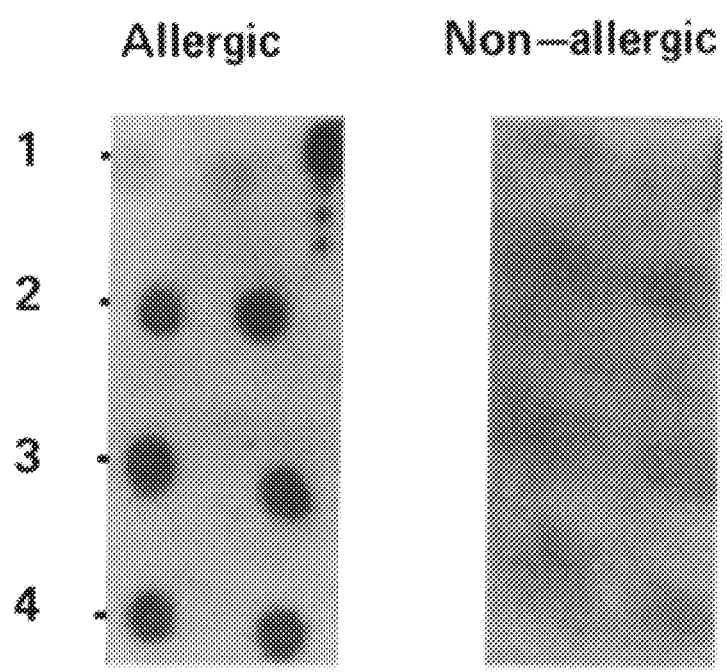
FIG. 5 shows reaction of clone pGEX-p1 (13T) with IgE in allergic serum. Overnight cultures of pGEX or pGEX-p1 where diluted 1/10 in broth and grown for 2 hours at 37° C. They were induced with IPTG, grown for 2 hours at 37° C.

The DNA insert from λgt11 p1(13T) which codes for Der p I was subcloned into the EcoRI site of the plasmid expression vector (pGEX)(26) where it could be expressed as a fusion with a glutathione transferase molecule. E. coli infected with this plasmid pGEX-p1(13T) or with the vector alone were grown to a log phase culture and harvested by centrifugation. The bacteria were suspended in PBS to 1/20 of their culture volume and lysed by freeze-thawing. The lysate was shown by sodium dodecyl-sulphate polyacrylamide electrophoresis to express a fusion protein in high concentration of the expected Mr 50,000. These lysates were then tested for their ability to react with IgE from allergic serum by radioimmune dot-blot conducted by the method described by Thomas and Rossi (27). The serum was taken from donors known to be mite-allergic or from non-allergic controls. Reactivity was developed by $^{125}I$-monoclonal anti-IgE and autoradiography. FIG. 5 shows the lysate from pGEX-p1(13T), but not the vector control reacted with IgE in allergic serum, but not non allergic serum.

EXAMPLE 3

Inhibition of IgE antibody responses to Der p I by treatment with the product from a cDNA clone coding for Der p I E. coli lysogenized by λgt11 p1(13T) were grown and induced by temperature switch to produce a recombinant fusion protein which was consistent with a 24 kD Der p I moiety and a 116 kD β-galactosidase moiety (p1(13T) (28). This protein was mostly insoluble and could be isolated to about 90% purity, judged by sodium didodecyl polyacrylamide electrophoresis, by differential centrifugation. A similar protein was produced from another gt11 cDNA mite clone λgt pX (2c). To test for the ability of the recombinant protein to modify IgE antibody responses to Der p I, groups of 4–5 CBA mice were injected intraperitoneally with 2 mg of the p1(13T) or pX (2c) fusion proteins and after 2 days given a subcutaneous injection of 5 µg of native Der p I (from mite culture medium) in aluminium hydroxide gel. The IgE antibody titres were measured by passive cutaneous anaphylaxis (PCA) after 3 and 6 weeks. The methods and background data for these responses have been described by Stewart and Holt (29). For a specificity control, groups of mice injected with p1(13T) or pX (2c) were also injected with 10 µg of ovalbumin in alum. Responses were compared to mice without prior p1(13T) or pX (2c) treatment (Table 1). After 3 weeks mice either not given an injection of recombinant protein or injected with the control pX (2c) had detectable anti Der p I PCA titres (1/2 or greater). Only 1/5 of mice treated with recombinant p1(13T) had a detectable titre and this at 1/4 was lower than all of the titres of both control groups. Titres of all groups at 6 weeks were low or absent (not shown). The PCA response to ovalbumin was not significantly affected by treatment with recombinant proteins. These data show the potential of the recombinant proteins to specifically decrease IgE responses as required for a desensitizing agent.

TABLE 1

Inhibition of anti-Der p I IgE by preinjection with with recombinant Der p I.

| group | preinjection −2 days | immunizing injection (d0) (5 μg/alum) | IgE (PCA) titres at d21 responders | titres |
|---|---|---|---|---|
| 1 | — | Der p I | 4/4 | 1/16–1/64 |
| 2 | pX(2C) | Der p I | 5/5 | 1/8–1/16 |
| 3 | p1(13T) | Der p I | 1/5* | 1/4* |
| 4 | — | ovalbumin | 4/4 | 1/64–1/256 |
| 5 | pX(2C) | ovalbumin | 5/5 | 1/32–1/128 |
| 6 | p1(13T) | ovalbumin | 5/5 | 1/64–1/256 |

*Mann Whitney analysis.

mice were given a preinjection on day −2 and then immunized with Der p I or ovalbumin on day 0. Serum antibody titres were measured on day 21 and 42 by PCA in rat skin. Significant anti-Der p I titres were not detected on day 42 (not shown). The PCA were measured to Der p I for groups 1–3 and ovalbumin for groups 4–6. The anti-Der p I titres were lower (p<0.001)* when pretreated with recombinant Der p I p1(13T).

EXAMPLE 4

Expression of Der p I antigenic determinants by fragments of the cDNA from λgt11 p1(13T)

The cDNA from λgt11 (13T) coding for Der p I was fragmented by sonication. The fragments (in varying size ranges) were isolated by electrophoresis, filled in by the Klenow reaction to create blunt ends. EcoRI linkers were attached and the fragment libraries cloned in λgt11. The methods used for the fragments cloning were the same as that used for cDNA cloning (6). Plaque immunoassay was used for screening with rabbit anti-Der p I. Three phage clones reacting with the antiserum were isolated and the oligonucleotide sequences of the cloned fragments obtained. Two of these were found to code for Der p I amino acids 17–55 (see FIG. 1 for numbering) and one for amino acids 70–100. Such fragments will eventually be useful for both diagnostic reagents to determine epitope reactivity and for therapy where molecules of limited allergenicity may increase safety of desensitisation.

EXAMPLE 5

Cloning and expression of cDNA coding for the major mite allergen Der p II

The Dermatophagoides pteronyssinus cDNA library in λgt11 previously described was screened by plaque radio-immune assay using nitrocellulose lifts (6). Instead of using specific antisera the sera used was from a person allergic to house dust mites. The serum (at ½ dilution) was absorbed with E. coli. To detect reactivity an $^{125}$I labelled monoclonal anti-IgE was used (at 30 ng/ml with $2 \times 10^6$ cpm/ml (approx. 30% counting efficiency)). After 1 hour the filters were washed and autoradiography performed. Using this procedure 4 clones reacting with human IgE were isolated. It was found they were related by DNA hybridization and had an identical pattern of reactivity against a panel of allergic sera. FIG. 6 shows IgE reactivity in plaque radioimmunoassay against allergic serum (AM) (top row) or non allergic (WT). Here, clones 1, 3 and 8 react strongly, but only against allergic sera. The amp 1 segments (present in row 1) are a λgt11 vector control. The bottom row is an immunoassay with rabbit anti-Der p I, developed by $^{125}$I staphylococcus protein A which shows no significant reactivity. The clones were tested against a panel of sera. Serum from five patients without allergy to mite did not react, but serum from 14/17 people with mite allergy showed reactivity. The DNA insert from the clone λgt11 pII(C1) was subcloned into M13 mp18 and M13 mp19 and sequenced by the chain termination method. The nucleotide sequence (FIG. 7) showed this allergen was Der p II by (a) the homology of the inferred amino acid sequence of residues 1–40 with that of the N-terminal amino acid of Der p II (30); and (b) the homology of this sequence with the equivalent Der f II allergen from Dermatophagoides farinae (30).

EXAMPLE 6

Isolation and Characterization of cDNA Coding for Der f I

MATERIALS AND METHODS

Dermatophagoides farinae culture

Mites were purchased from Commonwealth Serum Laboratories, Parkville, Australia.

Construction of the D. farinae cDNA λgt11 library

Polyadenylated mRNA was isolated from live D. farinae mites and cDNA was synthesized by the RNase H method (Gubler, V. and B. J. Hoffman, Gene 25:263–269 (1983)) using a kit (Amersham International, Bucks.). After the addition of EcoRI linkers (New England Biolabs, Beverly, Mass.) the cDNA was ligated to alkaline phosphatase treated λgt11 arms (Promega, Madison, Wis,). The ligated DNA was packaged and plated in E. coli Y1090 (r−) to produce a library of $2 \times 10^4$ recombinants.

Isolation of Der f I cDNA clones from the D. farinae cDNA λgt11 library

Screening of the library was performed by hybridization with two probes comprising the two Der p I cDNA BamHI fragments 1–348 and 349–857 generated by BamHI digestion of a derivative of the Der p I cDNA which has had two BamHI restriction sites inserted between amino acid residues −1 and 1 and between residues 116 and 117 by site-directed mutagenesis (Chua, K. Y. et al., J. Exp. Med. 167:175–182 (1988)). The probes were radiolabelled with $^{32}$P by nick translation. Phage were plated at 20,000 pfu per 150 mm petri dish and plaques were lifted onto nitrocellulose (Schleicher and Schull, Dassel, FRG), denatured and baked (Maniatis, T. et al., Molecular Cloning: A Laboratory Manual, Cold Spring Harbor Laboratory Press (1982)). Prehybridizations were performed for 2 hours at 42° C. in 50% formamide/5×SSCE/1×Denhardt's/poly C (0.1 mg/ml) /poly U(0.1 mg/ml) with hybridization overnight at 42° C. at $10^6$ cpm/ml. Post hybridization washes consisted of 15 min washes at room temperature with 2× sodium chloride citrate (SSC)/0.1% sodium dodecylsulphate (SDS), 0.5×SSC/0.1% SDS, 0.1×SSC/0.1% SDS successively and a final wash at 50° C. for 30 min in 0.1×SSC/1% SDS.

Isolation of DNA from λgt11 f 1 cDNA clones

Phage DNA from λgt11 f 1 clones was prepared by a rapid isolation procedure. Clarified phage plate lysate (1 ml) was mixed with 270 of 25% wt/vol polyethylene glycol (PEG 6000) in 2.5M NaCl and incubated at room temperature for 15 min. The mixture was then spun for 5 min in a microfuge (Eppendorf, FRG), and the supernatant was removed. The pellet was dissolved in 100 μL of 10 mM Tris/HCl pH8.0 containing 1 mM EDTA and 100 mM NaCl (TE). This DNA preparation was extracted with phenol/TE, the phenol phase was washed with 100 μl TE, the pooled aqueous phases were then extracted another 2 times with phenol/TE, 2 times with Leder phenol (phenol/chloroform/isoamylalcohol; 25:24:1), once with chloroform and the DNA was precipitated by ethanol.

DNA sequencing

To obtain clones for DNA sequence analysis, the λgt11 f1 phage DNA was digested with EcoRI restriction enzyme (Pharmacia, Uppsala, Sweden) and the DNA insert was ligated to EcoRI-digested M13-derived sequencing vectors mp18 and mp19 (Maniatis, T. et al., *Molecular Cloning: A Laboratory Manual,* Cold Spring Harbor Laboratory Press (1982)). Transformation was carried out using *E. coli* TG-1 and sequencing was performed by the dideoxynucleotide chain termination method (Sanger, F. et al., *Proc. Natl. Acad. Sci. USA,* 74:5463–5467 (1977)) using the Sequenase version 2.0 DNA sequencing kit (U.S.B., Cleveland, Ohio).

Polymerase chain reaction (PCR)

PCR was performed by the Taq DNA polymerase method (Saiki, R. K. et al., *Science* 239:487–491 (1988)) using the TaqPaq kit (Biotech International, Bentley, Wash.) and the conditions recommended by the supplier with long of target DNA and 10 pmol of λgt11 primers (New England BioLabs, Beverly, Mass.).

RESULTS

Isolation of *Der f* I cDNA clones

Two clones expressing the major mite allergen *Der f* I were isolated from the *D. farinae* cDNA λgt11 library by their ability to hybridize with both of the *Der p* I cDNA probes (nucleotides 1–348 and 349–857). This approach was adopted because amino acid sequencing had shown high homology (80%) between these two allergens (Thomas, W. R., et al., *Advances in the Biosciences,* 14:139–147 (1989)). Digestion of the λgt11 f1 clone DNA with EcoRI restriction enzyme to release the cDNA insert produced three *Der f* I cDNA EcoRI fragments: one approximately 800 bases long and a doublet approximately 150 bases long. The *Der f* I cDNA insert was also amplified from the phage DNA by the polymerase chain reaction (PCR) resulting in a PCR product of approximately 1.1-kb. Each *Der f* I cDNA fragment was cloned separately into the M13-derived sequencing vectors mp18 and mp19 and sequenced.

DNA sequence analysis

The nucleotide sequence of *Der f* I cDNA was determined using the sequencing strategy shown in FIG. 9. The complete sequence was shown to be 1084 bases long and included a 335-base long 5' proximal end sequence, a coding region for the entire native *Der f* I protein of 223 amino acids with a derived molecular weight of 25,191 and an 80-base long 3' noncoding region (FIG. 10). The assignment of the threonine residue at position 1 as the $NH_2$-terminal amino acid of *Der f* I was based on data obtained by $NH_2$-terminal amino acid sequencing of the native protein and the predicted amino acid sequence of recombinant *Der p* I (Chua, K. Y. et al., *J. Exp. Med.,* 167:175–182 (1988)). The predicted amino acid sequence of the *Der f* I cDNA in the $NH_2$-terminal region matched completely with that determined at the protein level (FIG. 10).

The complete mature protein coded by a single open reading frame terminating at the TGA stop codon at nucleotide position 42-44 is presumed to be the translation initiation site since the subsequent sequence codes for a typical signal peptide sequence.

Amino Acid Sequence Analysis

The amino acid sequence of *Der f* I predicted by nucleotide analysis is shown in FIG. 10. As shown in the composite alignment of the amino acid sequence of mature *Der p* I and *Der f* I (FIG. 11), high homology was observed between the two proteins. Sequence homology analysis revealed that the *Der f* I protein showed 81% homology with the *Der p* I protein as predicted by previous conventional amino acid sequencing. In particular, the residues making up the active side of *Der p* I, based on those determined for papain, actinidin, cathepsin H, and cathepsin B, are also conserved in the *Der f* I protein. The residues are glutamine (residue 29), glycine, serine and cysteine (residues 33–35), histidine (residue 171) and asparagine, serine and tryptophan (residues 191–193) where the numbering refers to *Der f* I. The predicted mature *Der f* I amino acid sequence contains a potential N-glycosylation site (Asn-Thr-Ser) at position 53–55 which is also present as Asn-Gln-Ser at the equivalent position in *Der p* I.

Analysis of the predicted amino acid sequence of the entire *Der f* I cDNA insert has shown that, as for other cysteine proteases (FIG. 12), the *Der f* I protein has pre- and proform intermediates. As previously mentioned, the methionine residue at position –98 is presumed to be the initiation methionine. This assumption is based on the fact that firstly, the 5' proximal end sequence from residues –98 to –81 is composed predominantly of hydrophobic amino acid residues (72%), which is the characteristic feature of signal peptides (Von Heijne, G., *EMBO J.,* 3:2315–2323 (1984)). Secondly, the lengths of the presumptive pre- (18 amino acid residues) and pro-peptides (80 residues) are similar to those for other cysteine proteases (FIG. 12). Most cysteine proteases examined have about 120 preproenzyme residues (of which an average of 19 residues form the signal peptide) with cathepsin B the smallest with 80 (Ishidoh, K. et al., *FEBS Letters,* 226:32–37 (1987)). *Der f* I falls within this range with a total of 98 preproenzyme residues.

By following the method for predicting signal-sequence cleavage sites outlined in Von Heijne, it is proposed that cleavage from the pre-*Der f* I sequence for proenzyme formation occurs at the signal peptidase cleavage site lying between Ala (–81) and Arg (–80) (Von Heijne, G., *Eur. J. Biochem.,* 133:17–21 (1988) and *J. Mol. Biol.,* 184:99–105 (1985)). Thus, the sequence from residues –98 to –81 codes for the leader peptide while the proenzyme moiety of *Der f* I begins at residue Arg (–80) and ends at residue Glu (–1).

EXAMPLE 7

Isolation and Characterization of cDNA Coding for *Der f* II

MATERIALS AND METHODS

Amino acid sequence analysis

Preparation of λgt11 *D. farinae* cDNA ligations

*D. farinae* was purchased from Commonwealth Serum Laboratories, Parkville, Australia, and used to prepare mRNA (polyadenylated RNA) as described (Stewart, G. A. and W. R. Thomas, *Int. Arch. Allergy Appl Immunol.,* 83:384–389 (1987)). The mRNA was suspended at approximately 0.5 μg/μl and 5 μg used to prepare cDNA by the RNase H method (Gubler, U. and Hoffman, B. J., *Gene,* 25:263–269 (1983)) using a kit (Amersham International, Bucks). EcoRI linkers (Amersham, GGAATTCC) were attached according to the method described by Huynh et al., Constructing and screening cDNA libraries in gt10 and gt11, In: Glover, DNA Cloning vol. A practical approach pp. 47–78 IRL Press, Oxford (1985)). The DNA was then digested with EcoRI and recovered from an agarose gel purification by electrophoresis into a DEAE membrane (Schleicher and Schuell, Dassel, FRG, NA-45) according to protocol 6.24 of Sambrook et al., (Sambrook et al., Molecular Cloning: A Laboratory Manual, 2d Ed., Cold Spring Harbor Laboratory Press (1989)), except 0.5M arginine base was used for elution. The cDNA was then ligated in λgt10 and λgt11 at an arms to insert ratio of 2:1. Some was packaged for plaque libraries and an aliquot retained for isolating sequences by polymerase chain reaction as described below.

Isolation of Der f II cDNA by Polymerase Chain Reaction

To isolate Der f II cDNA, an oligonucleotide primer based on the N-terminal sequence of Der p II was made because their amino acid residues are identical in these regions (Heymann, P. W. et al., J. Allergy Clin. Immunol., 83:1055–1087 (1989)). The primer GGATCCGATCAACTCGATGC-3' was used. The first GGATCC encodes a BamH1 site and the following sequence GAT . . . encodes the first four residues of Der p II. For the other primer the λgt11 TTGACACCAGACCAACTGGTAATG-3' reverse primer flanking the EcoRI cloning site was used (New England Biolabs, Beverly, Mass.). The Der p II primer was designed to have approximately 50–60% G–C and to end on the first or second, rather than the third, base of a codon (Gould, S. J. et al., Proc. Natl. Acad. Sci., 86:1934–1938 (1989); Summer, R. and D. Tautz, Nucleic Acid Res., 17:6749 (1989)).

The PCR reactions were carried out in a final reaction volume of 25 μl containing 67 mM Tris-HCL (pH8.8 at 25° C.), 16.6 mM $(NH_4)_2SO_4$, 40 μM dNTPs, 5 mM 2-mercaptoethanol, 6 μM EDTA, 0.2 mg/ml gelatin, 2 mM $MgCl_2$, 10 pmoles of each primer and 2 units of Taq polymerase. Approximately 0.001 μg of target DNA was added and the contents of the tube were mixed and overlayed with paraffin oil. The tubes were initially denatured at 95° C. for 6 minutes, then annealed at 55° C. for 1 minute and extended at 72° C. for 2 minutes. Thereafter for 38 cycles, denaturing was carried out for 30 seconds and annealing and extension as before. In the final (40th) cycle, the extension reaction was increased to 10 minutes to ensure that all amplified products were full length. The annealing temperature was deliberately set slightly lower than the Tm of the oligonucleotide primers (determined by the formula Tm=69.3+0.41 (G+C%)−650/oligo length) to allow for mismatches in the N-terminal primer.

5 μl of the reaction was then checked for amplified bands on a 1% agarose gel. The remainder of the reaction mixture was extracted with chloroform to remove all of the paraffin oil and ethanol precipitated prior to purification of the amplified product on a low melting point agarose gel (Bio-Rad, Richmond, Calif.).

Subcloning of PCR Product

The ends of the purified PCR product were filled in a reaction containing 10 mM Tris HCl, 10 mM $MgCl_2$, 50 mM NaCl, 0.025 mM dNTP and 1 μl of Klenow enzyme in a final volume of 100 μl. The reaction was carried out at 37° C. for 15 minutes and heat inactivated at 70° C. for 10 minutes. The mixture was Leder phenol extracted before ethanol precipitation. The resulting blunt ended DNA was ligated into M13mp118 digested with Sma I in a reaction containing 0.5M ATP, 1× ligase buffer and 1 unit of $T_4$ ligase at 15° C. for 24 hrs and transformed into E. coli TG1 made competent by the $CaCl_2$ method. The transformed cells were plated out as a lawn on L+G plates and grown overnight at 37° C.

Preparation of Single-stranded DNA Template for Sequencing

Isolated white plaques were picked using an orange stick into 2.5 ml of an overnight culture of TG1 cells diluted 1 in 100 in 2× TY broth, and grown at 37° C. for 6 hours. The cultures were pelleted and the supernatant removed to a fresh tube. To a 1 ml aliquot of this supernatant 270 μl of 20% polyethylene glycol, 2.5M NaCl was added and the tube was vortexed before allowing it to stand at room temperature (RT) for 15 minutes. This was then spun down again and all traces of the supernatant were removed from the tube. The pellet was then resuspended in 100 μl of 1× TE buffer. At least 2 phenol:TE extractions were done, followed by 1 Leder phenol extraction and a $CHCl_3$ extraction. The DNA was precipitated in ethanol and resuspended in a final volume of 20 μl of TE buffer.

DNA Analysis

DNA sequencing was performed with the dideoxynucleotide chain termination (Sanger, F. et al., Proc. Natl. Acad. Sci., 74:5463–5467 (1977)) using DNA produced from M13 derived vectors mp18 and mp19 in E. coli TG1 and T4 DNA polymerase (Sequenase version 2.0, USB Corp., Cleveland, Ohio; Restriction endonucleases were from Toyobo, (Osaka, Japan). All general procedures were by standard techniques (Sambrook, J. et al., A Laboratory Manual, 2d Ed. Cold Spring Harbor Laboratory Press (1989)). The sequence analysis was performed using the Mac Vector Software (IBI, New Haven, Conn.).

RESULTS

D. farinae cDNA ligated in λgt11 was used to amplify a sequence using an oligonucleotide primer with homology to nucleotides coding for the 4 N-terminal residues of Der p II and a reverse primer for the λgt11 sequence flanking the coding site. Two major bands of about 500 bp and 300 bp were obtained when the product was gel electrophoresed. These were ligated into M13 mp18 and a number of clones containing the 500 bp fragment were analyzed by DNA sequencing. Three clones produced sequence data from the N-terminal primer end and one from the other orientation. Where the sequence data from the two directions overlapped, a complete match was found. One of the clones read from the N-terminal primer, contained a one-base deletion which shifted the reading frame. It was deduced to be a copying error, as the translated sequence from the other two clones matched the protein sequence for the first 20 amino acid residues of the allergen.

The sequence of the clones showing consensus and producing a correct reading frame is shown in FIG. 14, along with the inferred amino acid sequence. It coded for a 129 residue protein with no N-glycosylation site and a calculated molecular weight of 14,021 kD. No homology was found when compared to other proteins on the GenBank data base (61.0 release). It did, however, show 88% amino acid residue homology with Der p II shown in the alignment in FIG. 16. Seven out of the 16 changes were conservative. The conserved residues also include all the cysteines present at positions 8, 21, 27, 73 and 119. There was also considerable nucleotide homology, although the restriction enzyme map generated from the sequence data for commonly used enzymes is different from Der p II (FIG. 15). The hydrophobicity plots of the translated sequence of Der f II and Der p II shown in FIG. 17 are almost identical.

EXAMPLE 8

Determination of Nucleotide Sequence Polymorphisms in the Der p I, Der p II and Der f II Allergens It was expected that there were sequence polymorphisms, in the nucleic acid sequence coding for Der p I, Der p II, Der ƒ I and *Der ƒ* II, due to natural allelic variation among individual mites. Several nucleotide and resulting amino acid sequence polymorphisms were discovered during the sequencing of different *Der p* I, *Der p* II and *Der ƒ* II clones. The amino acid sequence polymorphisms are shown in FIGS. 18, 19 and 20.

The original *Der p* I λgt11 cDNA library was reprobed with cDNA obtained from the λgt11 pI(13T) clone to identify new clones. Similarly, the λgt11 cDNA library of *Der p* II was reprobed with cDNA obtained from the λgt11 pII(C1) clone to identify additional *Der p* II clones. These clones were isolated, sequenced and found to contain nucleotide and resulting amino acid sequence polymorphisms (see FIG. 18 and 19).

Four *Der p* I clones, (b), (c), (d) and (e) were sequenced, as shown in FIG. 18. Clone *Der p* I(d) was found to contain the following polymorphisms relative to the clone *Der p* I(a) sequence: (1) the codon for amino acid residue 136 was ACC rather than AGC, which results in a predicted amino acid substitution of Thr for Ser; (2) the codon for amino acid residue 149 had a silent mutation, GCT rather than GCA; and (3) the codon for amino acid residue 215 was CAA rather than GAA; which results in a predicted amino acid substitution of Gln for Glu.

The *Der p* II clones, *Der p* II(1) and *Der p* II(2) were sequenced as shown in FIG. 19. Clone *Der p* II(2) was found to have the codon TCA, rather than ACA at amino acid residue 47, which results in a predicted amino acid substitution of Ser for Thr. This clone also was found to have the codon AAT at amino acid residue 113 rather than GAT, which results in a predicted amino acid substitution of Asn for Asp. The codon for amino acid 127 of this clone was found to be CTC rather than ATC. This change in codon 127 results in a predicted amino acid substitution of Leu for Ile.

Additional *Der ƒ* II cDNA clones containing nucleic acid and resulting amino acid sequence polymorphisms were obtained from PCR reactions using cDNA prepared with RNA isolated from *D. farinae* mites (Commonwealth Serum Laboratories, Parksville, Australia). cDNA was prepared and ligated in λgt10 as previously described (Trudinger e al. (1991) *Clin. Exp. Allergy* 21:33–37). The clones described below were isolated following PCR of the λgt10 library using a 5' primer, which had the sequence 5'-GGATCCGATCAAGTCGATGT-3'. The nucleotides 5'-GGATCC-3' of the 5' primer correspond to a Bam HI endonuclease site added for cloning purposes. The remaining nucleotides of the 5' primer, 5'-GATCAAGTCGATGT-3' correspond to the first 4 amino acids of *Der p* II (Chua et al. (1990) *Int. Arch. Allergy Clin. Immunol.* 91:118–123) as described in Trudinger et al. ((1991) *Clin. Exp. Allergy* 21:33–37). The 3' primer, which has the sequence 5'-TTGACACCAGACCAACTGGTAATG-3', corresponds to a sequence of the λgt10 cloning vector (Trudinger et al. supra).

PCR was performed as described (Trudinger et al. supra) and four *Der ƒ* II clones, MT3, MT5, MT16 and MT18, were sequenced, as shown in FIG. 20. Three clones were sequenced that had potential polymorphisms relative to the published *Der ƒ* II sequence (Trudinger et al. supra). The codon for amino acid 52 of clone MT18 was ATT rather than the published ACT (Trudinger et al. supra). This change in codon 52 of clone MT18 would result in a predicted amino acid change from Thr to Ile. Clone MT5 contained three changes from the published sequence (Trudinger et al. supra): (1) the codon for amino acid 11 was AGC rather than the published AAC (Trudinger et al. supra), which results in a predicted amino acid substitution of Ser for Asn; (2) the codon for amino acid 52 was ATT, rather than the published ACT (Trudinger et al. supra), which results in a predicted amino acid substitution of Ile for Thr; and (3) the codon for amino acid 88 was ATC rather than the published GCC (Trudinger et al. supra), which results in a predicted amino acid substitution of Ile for Ala. Clone MT16 had a silent mutation in the codon for amino acid 68 (ATC versus the published ATT (Trudinger et al. supra) that did not change the predicted amino acid at this residue. The following substitutes were also observed by Yuuki et al. (*Jpn.J.Allergol.* 6:557–561, 1990); Ile at residue 52, Ile at residue 54 and Ile at residue 88.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

1. Ford, A. W., Rawle, F. C., Lind, P., Spieksma, F. T. M., Lowenstein, H., Platts-Mills, T. A. E. (1985). Standardization of *Dermatophagoides Pteronyssinus*. Assessment of potency and allergen content in the coded extracts. *Int. Arch. Allergy Appl. Immunol.* 76:58–67.
2. Lind, P., Lowenstein, H. (1983). Identification of allergens in *Dermatophagoides pteronyssinus* mite body extract by crossed radioimmunelectrophoresis with two different rabbit antibody pools. *Scand. J. Immunol.* 17:263–273.
3. Krilis, S., Baldo, B. A., Basten, A. (1984). Antigens and allergens from the common house dust mite *Dermatophagoides pteronyssinus* Part II. Identification of the major IgE binding antigens by crossed radioimmunoelectrophoresis. *J. Allergy Clin. Immunol.* 74:142–146.
4. Tovey, E. R., Chapman, M. D., Platts-Mills, T. A. E. (1981). Mite faeces are a major source of house dust allergens. *Nature* 289:592–593.
5. Gubler, U., Hoffman, B. J. (1983). A simple and very efficient method for generating cDNA libraries. *Gene* 25:263–269.
6. Huynh, T. V., Young, R. A., Davis, R. W. Constructing and screening cDNA libraries in λ10 and λgt11. p48–78 in DNA Cloning Col. 1, A practical approach. Ed. D. M. Glover, IRL press.
7. Stewart, G. A., Thomas, W. R. (1987). In vitro translation of messenger RNA from the house mite *Dermatophagoides pteronyssinus*. *Int. Arch. Allergy Appl. Immunol.* 83:384–389.
8. Thomas, W. R., Rossi, A. A. (1986). Molecular cloning of DNA coding for outer membrane proteins of *Haemophilus influenzae* type b. *Infection and Immunity* 52:812–817.
9. Simpson, R. J., Smith, J. A., Mortiz, R. L., O'Hare, M. J., Rudland, P. S., Morrison, J. R., Lloyd, C. J., Grego, B., Burgess, A. W. and Nice, E. L. (1985). Rat Epidermal Growth Factor: Complete amino acid sequence. *Eur. J. Biochem.* 153:629–637.
10. Maniatis, T., Fritsch, E. F., Sambrook, J. (1982). Molecular cloning. A Laboratory Manual, Cold Spring Harbor Laboratory.
11. Sanger, F., Nicklen, S., Coulson, A. R. (1977). DNA sequencing with chain-terminating inhibitors. *Proc. Natl. Acad. Sci.* 74:5463–5467.
12. Heyman, P. W., Chapman, M. D., Platts-Mills, T. A. E. (1986). Antigen *Der ƒ* I from the house dust mite *Dermatophagoides farinae:* Structural comparison with *Der p* I from *Dermatophagoides pteronyssinus* and epitope specificity of murine IgG and human IgE antibodies. *J. Immunol.* 137:2841–2847.
13. Voorhorst, R., Spieksma-Boezeman, M. I. A., and Spieksma, F. Th. M. (1964). Is a mite (Dermatophagoides sp) the producer of the house dust allergen. *Allerg. Asthma.* 10:329.
14. Voorhorst, R., Spieksma, F. Th. M., Varekamp, H., Leupen, M. J. and Lyklema, A. W., (1967). The house dust mite (*Dermatophagoides pteronyssinus*) and the allergens it produces. Identity with the house dust allergen. *J. Allergy.* 39:325.
15. Stewart, G. A. and Thomas, W. R. (1987). In vitro translation of messenger RNA from the house dust mite *Dermatophagoides pteronyssinus. Int. Arch. Allergy Appl. Immunol.* 83:384.
16. Messing, J. (1983). New M13 vectors for cloning. *Methods Enzymol.* 101:20.
17. Stewart, G. A., Simpson, R. J., Thomas, W. R. and Turner, K. J. (1986). The physiochemical characterization of a major protein allergen from the house dust mite, EP. *Asian Pac. J. Allergy Immunol.* 5:71.
18. Kozak, M. (1984). Compilation and analysis of sequences upstream from the translational start site in eukaryotic mRNAs. *Nucleic, Acids Res.* 12:857.
19. San Segundo, B., Chain, S. J. and Steiner, D. F. (1985). Identification of cDNA clones encoding a precursor of rat liver cathepsin B. *Proc. Natl. Acad. Sci. USA.* 82:2320.
20. Portnoy, D. A., Erickson, A. H., Kochan, J., Ravetch, J. V. and Unkeless, J. C. (1986). Cloning and characterization of a mouse cysteine proteinase. *J. Biol. Chem.* 261:14697.
21. Williams, J. G., North, M. J. and Mahbubani, H. (1985). A developmentally regulated cysteine proteinase in *Dictyostelium discoideum. EMBO (Eur. Mol. Biol. Organ.) J.* 4:999.
22. Hopp, T. P. (1986). Protein surface analysis. Method for identifying antigenic determinants and other interaction sites. *J. Immunol. Methods.* 88:1.
23. Von Heijne, G. (1984). Analysis of the distribution of charged residues in the N-terminal region of signal sequences: implications of protein export in prokaryotic and eukaryotic cells. *EMBO (Eur. Mol. Biol. Organ.) J.* 3:2315.
24. Ullrich, A., Shine, J., Chirgwin, J., Pictet, R., Tischer, E., Rutter, W. J. and Goodman, H. W. (1977). Rat insulin genes: Construction of plasmids containing th coding sequences. *Science (Wash. D.C.)* 196:1313.
25. Carne, T. and Scheele, G. (1985). Cell Biology of the Secretory Process. M. Cantin, editor. S. Karger AG, Basel. 73.
26. Smith, D. and Johnson (1988), *Gene* (in press).
27. Thomas, W. R. and Rossi, A. A. (1986). Molecular cloning of DNA coding for outer membrane proteins of *Haemophilus influenzae* Type b. *Infection and Immunity* 52:812–817.
28. Thomas, W. R., Stewart, G. A., Simpson, R. J., Chua, K. Y., Plozza, T. M., Dilworth, Dr. U., Nisbet, A. and Turner, K. J. (1987). Cloning and expression of DNA coding for the major house dust mite allergen *Der p* I in *Escherichia coli. Int. Arch. Allergy Appl. Immunol.* 83:127–129.
29. Stewart, G. A. and Holt, P. G. (1987). Immunogenicity and tolerogenicity of a major house dust mite allergen *Der p* I. *Int. Arch. Allergy Appl. Immunol.* 83:44–51.
31. Chapman, M. D., Heymann, P. W. and Platts-Mills, T. A. E. (1987). Mite allergens 1. Epitope mapping of major dust mite (Dermatophagoides) allergens using monoclonal antibodies. Mite Allergy—A World Wide Problem. Ed. A. L. deWeck and A. Todt. The UCB Institute of Allergy.

We claim:

1. An isolated peptide comprising a portion of a *Der p* I protein allergen having the following amino acid sequence (SEQ ID NO:11), wherein said portion comprises at least one T cell epitope and at least one amino acid sequence polymorphism selected from the group consisting of Xaa$_1$, Xaa$_2$, Xaa$_3$, Xaa$_4$, Xaa$_5$:

Thr Asn Ala Cys Ser Ile Asn Gly Asn Ala Pro Ala Glu Ile Asp Leu Arg Gln Met Arg Thr Val Thr Pro Ile Arg Met Gln Gly Gly Cys Gly Ser Cys Trp Ala Phe Ser Gly Val Ala Ala Thr Glu Ser Ala Tyr Leu Ala Xaa$_1$ Arg Asn Gln Ser Leu Asp Leu Ala Glu Gln Glu Leu Val Asp Cys Ala Ser Gln His Gly Cys His Gly Asp Thr Ile Pro Arg Gly Ile Xaa$_2$ Tyr Ile Gln His Asn Gly Val Val Gln Glu Ser Tyr Tyr Arg Tyr Val Ala Arg Glu Gln Ser Cys Arg Arg Pro Asn Ala Gln Arg Phe Gly Ile Ser Asn Tyr Cys Gln Ile Tyr Pro Pro Asn Xaa$_3$ Asn Lys Ile Arg Glu Ala Leu Ala Gln Thr His Xaa$_4$ Ala Ile Ala Val Ile Ile Gly Ile Lys Asp Leu Asp Ala Phe Arg His Tyr Asp Gly Arg Thr Ile Ile Gln Arg Asp Asn Gly Tyr Gln Pro Asn Tyr His Ala Val Asn Ile Val Gly Tyr Ser Asn Ala Gln Gly Val Asp Tyr Trp Ile Val Arg Asn Ser Trp Asp Thr Asn Trp Gly

Asp Asn Gly Tyr Gly Tyr Phe Ala Ala Asn Ile Asp Leu Met Met Ile Glu Xaa$_5$ Tyr Pro Tyr Val Val Ile Leu where Xaa$_1$ is selected from the group consisting of His and Tyr;

where Xaa$_2$ is selected from the group consisting of Glu and Lys;

where Xaa$_3$ is selected from the group consisting of Ala and Val;

where Xaa$_4$ is selected from the group consisting of Ser and Thr; and where Xaa$_5$ is selected from the group consisting of Glu and Gln, except for the amino acid sequence where Xaa$_1$ is His, Xaa$_2$ is Glu, Xaa$_3$ is Ala, Xaa$_4$ is Ser and Xaa$_5$ is Glu (SEQ ID NO:11).

2. A therapeutic composition comprising a peptide of claim 1 and a pharmaceutically acceptable carrier or diluent.

\* \* \* \* \*

UNITED STATES PATENT AND TRADEMARK OFFICE
CERTIFICATE OF CORRECTION

PATENT NO. : 5,770,202
DATED : June 23, 1998
INVENTOR(S) : Wayne R. Thomas and Kaw-Yan Chua It is certified that error appears in the above-identified patent and that said Letters Patent is hereby corrected as shown below:

On the Title page,
Item [30] Foreign Application Priority Data

Sep. 10, 1991 [PCT] PCT.................PCT/AU91/00417

Signed and Sealed this

First Day of September, 1998

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 834 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..738

( x i ) SEQUENCE DESCRIPTION: SEQ ID NO:1:

```
AAA  AAC  CGA  TTT  TTG  ATG  AGT  GCA  GAA  GCT  TTT  GAA  CAC  CTC  AAA  ACT           48
Lys  Asn  Arg  Phe  Leu  Met  Ser  Ala  Glu  Ala  Phe  Glu  His  Leu  Lys  Thr
-23            -20                      -15                      -10

CAA  TTC  GAT  TTG  AAT  GCT  GAA  ACT  AAC  GCC  TGC  AGT  ATC  AAT  GGA  AAT           96
Gln  Phe  Asp  Leu  Asn  Ala  Glu  Thr  Asn  Ala  Cys  Ser  Ile  Asn  Gly  Asn
          -5                      -1   1                 5

GCT  CCA  GCT  GAA  ATC  GAT  TTG  CGA  CAA  ATG  CGA  ACT  GTC  ACT  CCC  ATT          144
Ala  Pro  Ala  Glu  Ile  Asp  Leu  Arg  Gln  Met  Arg  Thr  Val  Thr  Pro  Ile
10                  15                       20                       25
```

| | | | | | | | | | | | | | | | | |
|---|---|---|---|---|---|---|---|---|---|---|---|---|---|---|---|---|
| CGT | ATG | CAA | GGA | GGC | TGT | GGT | TCA | TGT | TGG | GCT | TTC | TCT | GGT | GTT | GCC | 192 |
| Arg | Met | Gln | Gly | Gly | Cys | Gly | Ser | Cys | Trp | Ala | Phe | Ser | Gly | Val | Ala | |
| | | | | 30 | | | | 35 | | | | | | 40 | | |
| GCA | ACT | GAA | TCA | GCT | TAT | TTG | GCT | CAC | CGT | AAT | CAA | TCA | TTG | GAT | CTT | 240 |
| Ala | Thr | Glu | Ser | Ala | Tyr | Leu | Ala | His | Arg | Asn | Gln | Ser | Leu | Asp | Leu | |
| | | | 45 | | | | | 50 | | | | | 55 | | | |
| GCT | GAA | CAA | GAA | TTA | GTC | GAT | TGT | GCT | TCC | CAA | CAC | GGT | TGT | CAT | GGT | 288 |
| Ala | Glu | Gln | Glu | Leu | Val | Asp | Cys | Ala | Ser | Gln | His | Gly | Cys | His | Gly | |
| | | 60 | | | | | 65 | | | | | 70 | | | | |
| GAT | ACC | ATT | CCA | CGT | GGT | ATT | GAA | TAC | ATC | CAA | CAT | AAT | GGT | GTC | GTC | 336 |
| Asp | Thr | Ile | Pro | Arg | Gly | Ile | Glu | Tyr | Ile | Gln | His | Asn | Gly | Val | Val | |
| | 75 | | | | | 80 | | | | | 85 | | | | | |
| CAA | GAA | AGC | TAC | TAT | CGA | TAC | GTT | GCA | CGA | GAA | CAA | TCA | TGC | CGA | CGA | 384 |
| Gln | Glu | Ser | Tyr | Tyr | Arg | Tyr | Val | Ala | Arg | Glu | Gln | Ser | Cys | Arg | Arg | |
| 90 | | | | | 95 | | | | | 100 | | | | | 105 | |
| CCA | AAT | GCA | CAA | CGT | TTC | GGT | ATC | TCA | AAC | TAT | TGC | CAA | ATT | TAC | CCA | 432 |
| Pro | Asn | Ala | Gln | Arg | Phe | Gly | Ile | Ser | Asn | Tyr | Cys | Gln | Ile | Tyr | Pro | |
| | | | | 110 | | | | | 115 | | | | | 120 | | |
| CCA | AAT | GCA | AAC | AAA | ATT | CGT | GAA | GCT | TTG | GCT | CAA | ACC | CAC | AGC | GCT | 480 |
| Pro | Asn | Ala | Asn | Lys | Ile | Arg | Glu | Ala | Leu | Ala | Gln | Thr | His | Ser | Ala | |
| | | | 125 | | | | | 130 | | | | | 135 | | | |
| ATT | GCC | GTC | ATT | ATT | GGC | ATC | AAA | GAT | TTA | GAC | GCA | TTC | CGT | CAT | TAT | 528 |
| Ile | Ala | Val | Ile | Ile | Gly | Ile | Lys | Asp | Leu | Asp | Ala | Phe | Arg | His | Tyr | |
| | | 140 | | | | | 145 | | | | | 150 | | | | |
| GAT | GGC | CGA | ACA | ATC | ATT | CAA | CGC | GAT | AAT | GGT | TAC | CAA | CCA | AAC | TAT | 576 |
| Asp | Gly | Arg | Thr | Ile | Ile | Gln | Arg | Asp | Asn | Gly | Tyr | Gln | Pro | Asn | Tyr | |
| | 155 | | | | | 160 | | | | | 165 | | | | | |
| CAC | GCT | GTC | AAC | ATT | GTT | GGT | TAC | AGT | AAC | GCA | CAA | GGT | GTC | GAT | TAT | 624 |
| His | Ala | Val | Asn | Ile | Val | Gly | Tyr | Ser | Asn | Ala | Gln | Gly | Val | Asp | Tyr | |
| 170 | | | | | 175 | | | | | 180 | | | | | 185 | |
| TGG | ATC | GTA | CGA | AAC | AGT | TGG | GAT | ACC | AAT | TGG | GGT | GAT | AAT | GGT | TAC | 672 |
| Trp | Ile | Val | Arg | Asn | Ser | Trp | Asp | Thr | Asn | Trp | Gly | Asp | Asn | Gly | Tyr | |
| | | | | 190 | | | | | 195 | | | | | 200 | | |
| GGT | TAT | TTT | GCT | GCC | AAC | ATC | GAT | TTG | ATG | ATG | ATT | GAA | GAA | TAT | CCA | 720 |
| Gly | Tyr | Phe | Ala | Ala | Asn | Ile | Asp | Leu | Met | Met | Ile | Glu | Glu | Tyr | Pro | |
| | | | 205 | | | | | 210 | | | | | 215 | | | |
| TAT | GTT | GTC | ATT | CTC | TAAACAAAAA | GACAATTTCT | TATATGATTG | TCACTAATTT | | | | | | | | 775 |
| Tyr | Val | Val | Ile | Leu | | | | | | | | | | | | |
| | | 220 | | | | | | | | | | | | | | |

ATTTAAAATC AAAATTTTTT AGAAAATGAA TAAATTCATT CACAAAAATT AAAAAAAA    834

( 2 ) INFORMATION FOR SEQ ID NO:2:

( i ) SEQUENCE CHARACTERISTICS:
    ( A ) LENGTH: 245 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Lys | Asn | Arg | Phe | Leu | Met | Ser | Ala | Glu | Ala | Phe | Glu | His | Leu | Lys | Thr |
| -23 | | | -20 | | | | | -15 | | | | | -10 | | |
| Gln | Phe | Asp | Leu | Asn | Ala | Glu | Thr | Asn | Ala | Cys | Ser | Ile | Asn | Gly | Asn |
| | | -5 | | | | | -1 | 1 | | | | 5 | | | |
| Ala | Pro | Ala | Glu | Ile | Asp | Leu | Arg | Gln | Met | Arg | Thr | Val | Thr | Pro | Ile |
| 10 | | | | | 15 | | | | | 20 | | | | | 25 |
| Arg | Met | Gln | Gly | Gly | Cys | Gly | Ser | Cys | Trp | Ala | Phe | Ser | Gly | Val | Ala |
| | | | | 30 | | | | 35 | | | | | | 40 | |
| Ala | Thr | Glu | Ser | Ala | Tyr | Leu | Ala | His | Arg | Asn | Gln | Ser | Leu | Asp | Leu |

```
                    45                          50                          55
Ala  Glu  Gln  Glu  Leu  Val  Asp  Cys  Ala  Ser  Gln  His  Gly  Cys  His  Gly
          60                       65                       70

Asp  Thr  Ile  Pro  Arg  Gly  Ile  Glu  Tyr  Ile  Gln  His  Asn  Gly  Val  Val
     75                            80                       85

Gln  Glu  Ser  Tyr  Tyr  Arg  Tyr  Val  Ala  Arg  Glu  Gln  Ser  Cys  Arg  Arg
90                       95                       100                      105

Pro  Asn  Ala  Gln  Arg  Phe  Gly  Ile  Ser  Asn  Tyr  Cys  Gln  Ile  Tyr  Pro
               110                       115                      120

Pro  Asn  Ala  Asn  Lys  Ile  Arg  Glu  Ala  Leu  Ala  Gln  Thr  His  Ser  Ala
               125                      130                      135

Ile  Ala  Val  Ile  Ile  Gly  Ile  Lys  Asp  Leu  Asp  Ala  Phe  Arg  His  Tyr
          140                      145                      150

Asp  Gly  Arg  Thr  Ile  Ile  Gln  Arg  Asp  Asn  Gly  Tyr  Gln  Pro  Asn  Tyr
     155                           160                      165

His  Ala  Val  Asn  Ile  Val  Gly  Tyr  Ser  Asn  Ala  Gln  Gly  Val  Asp  Tyr
170                      175                      180                      185

Trp  Ile  Val  Arg  Asn  Ser  Trp  Asp  Thr  Asn  Trp  Gly  Asp  Asn  Gly  Tyr
                190                      195                      200

Gly  Tyr  Phe  Ala  Ala  Asn  Ile  Asp  Leu  Met  Met  Ile  Glu  Glu  Tyr  Pro
               205                      210                      215

Tyr  Val  Val  Ile  Leu
               220
```

( 2 ) INFORMATION FOR SEQ ID NO:3:

( i ) SEQUENCE CHARACTERISTICS:
        ( A ) LENGTH: 588 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 69..509

( x i ) SEQUENCE DESCRIPTION: SEQ ID NO:3:

```
CACAAATTCT   TCTTTCTTCC   TTACTACTGA   TCATTAATCT   GAAAACAAAA   CCAAACAAAC      60

CATTCAAA  ATG  ATG  TAC  AAA  ATT  TTG  TGT  CTT  TCA  TTG  TTG  GTC  GCA  GCC     110
          Met  Tyr  Lys  Ile  Leu  Cys  Leu  Ser  Leu  Leu  Val  Ala  Ala
          -16  -15                 -10                              -5

GTT  GCT  CGT  GAT  CAA  GTC  GAT  GTC  AAA  GAT  TGT  GCC  AAT  CAT  GAA  ATC    158
Val  Ala  Arg  Asp  Gln  Val  Asp  Val  Lys  Asp  Cys  Ala  Asn  His  Glu  Ile
          -1   1              5                       10

AAA  AAA  GTT  TTG  GTA  CCA  GGA  TGC  CAT  GGT  TCA  GAA  CCA  TGT  ATC  ATT    206
Lys  Lys  Val  Leu  Val  Pro  Gly  Cys  His  Gly  Ser  Glu  Pro  Cys  Ile  Ile
          15                      20                      25

CAT  CGT  GGT  AAA  CCA  TTC  CAA  TTG  GAA  GCC  GTT  TTC  GAA  GCC  AAC  CAA    254
His  Arg  Gly  Lys  Pro  Phe  Gln  Leu  Glu  Ala  Val  Phe  Glu  Ala  Asn  Gln
30                       35                      40                       45

AAC  ACA  AAA  ACG  GCT  AAA  ATT  GAA  ATC  AAA  GCC  TCA  ATC  GAT  GGT  TTA    302
Asn  Thr  Lys  Thr  Ala  Lys  Ile  Glu  Ile  Lys  Ala  Ser  Ile  Asp  Gly  Leu
                    50                      55                       60

GAA  GTT  GAT  GTT  CCC  GGT  ATC  GAT  CCA  AAT  GCA  TGC  CAT  TAC  ATG  AAA    350
Glu  Val  Asp  Val  Pro  Gly  Ile  Asp  Pro  Asn  Ala  Cys  His  Tyr  Met  Lys
               65                      70                       75

TGC  CCA  TTG  GTT  AAA  GGA  CAA  CAA  TAT  GAT  ATT  AAA  TAT  ACA  TGG  AAT    398
Cys  Pro  Leu  Val  Lys  Gly  Gln  Gln  Tyr  Asp  Ile  Lys  Tyr  Thr  Trp  Asn
```

```
                                80                              85                              90
GTT  CCG  AAA  ATT  GCA  CCA  AAA  TCT  GAA  AAT  GTT  GTC  GTC  ACT  GTT  AAA        446
Val  Pro  Lys  Ile  Ala  Pro  Lys  Ser  Glu  Asn  Val  Val  Val  Thr  Val  Lys
     95                            100                           105

GTT  ATG  GGT  GAT  GAT  GGT  GTT  TTG  GCC  TGT  GCT  ATT  GCT  ACT  CAT  GCT        494
Val  Met  Gly  Asp  Asp  Gly  Val  Leu  Ala  Cys  Ala  Ile  Ala  Thr  His  Ala
110                           115                           120                      125

AAA  ATC  CGC  GAT  TAAATAAACA  AAATTTATTG  ATTTTGTAAT  CACAAATGAT                    546
Lys  Ile  Arg  Asp

TGATTTCTT  TCCAAAAAAA  AAATAAATAA  AATTTGGGA  AT                                      588
```

(2) INFORMATION FOR SEQ ID NO:4:

(i) SEQUENCE CHARACTERISTICS:
(A) LENGTH: 146 amino acids
(B) TYPE: amino acid
(D) TOPOLOGY: linear (ii) MOLECULE TYPE: protein (xi) SEQUENCE DESCRIPTION: SEQ ID NO:4:

```
Met  Met  Tyr  Lys  Ile  Leu  Cys  Leu  Ser  Leu  Leu  Val  Ala  Ala  Val  Ala
     -16  -15                      -10                           -5

Arg  Asp  Gln  Val  Asp  Val  Lys  Asp  Cys  Ala  Asn  His  Glu  Ile  Lys  Lys
-1        1                   5                        10                      15

Val  Leu  Val  Pro  Gly  Cys  His  Gly  Ser  Glu  Pro  Cys  Ile  Ile  His  Arg
               20                       25                            30

Gly  Lys  Pro  Phe  Gln  Leu  Glu  Ala  Val  Phe  Glu  Ala  Asn  Gln  Asn  Thr
                    35                       40                       45

Lys  Thr  Ala  Lys  Ile  Glu  Ile  Lys  Ala  Ser  Ile  Asp  Gly  Leu  Glu  Val
               50                       55                       60

Asp  Val  Pro  Gly  Ile  Asp  Pro  Asn  Ala  Cys  His  Tyr  Met  Lys  Cys  Pro
     65                       70                       75

Leu  Val  Lys  Gly  Gln  Gln  Tyr  Asp  Ile  Lys  Tyr  Thr  Trp  Asn  Val  Pro
80                       85                       90                           95

Lys  Ile  Ala  Pro  Lys  Ser  Glu  Asn  Val  Val  Thr  Val  Lys  Val  Met
                    100                      105                     110

Gly  Asp  Asp  Gly  Val  Leu  Ala  Cys  Ala  Ile  Ala  Thr  His  Ala  Lys  Ile
               115                      120                      125

Arg  Asp
```

(2) INFORMATION FOR SEQ ID NO:5:

(i) SEQUENCE CHARACTERISTICS:
(A) LENGTH: 1072 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 36..1001

(xi) SEQUENCE DESCRIPTION: SEQ ID NO:5:

```
CGTTTTCTTC  CATCAAAATT  AAAAATTCAT  CAAAA  ATG  AAA  TTC  GTT  TTG  GCC           53
                                          Met  Lys  Phe  Val  Leu  Ala
                                          -98            -95

ATT  GCC  TCT  TTG  TTG  GTA  TTG  AGC  ACT  GTT  TAT  GCT  CGT  CCA  GCT  TCA   101
Ile  Ala  Ser  Leu  Leu  Val  Leu  Ser  Thr  Val  Tyr  Ala  Arg  Pro  Ala  Ser
          -90                      -85                      -80
```

| | | | | | | | | | | | | | | | | |
|---|---|---|---|---|---|---|---|---|---|---|---|---|---|---|---|---|
| ATC | AAA | ACT | TTT | GAA | GAA | TTC | AAA | AAA | GCC | TTC | AAC | AAA | AAC | TAT | GCC | 149 |
| Ile | Lys | Thr | Phe | Glu | Glu | Phe | Lys | Lys | Ala | Phe | Asn | Lys | Asn | Tyr | Ala | |
| | -75 | | | | -70 | | | | -65 | | | | | | | |
| ACC | GTT | GAA | GAG | GAA | GAA | GTT | GCC | CGT | AAA | AAC | TTT | TTG | GAA | TCA | TTG | 197 |
| Thr | Val | Glu | Glu | Glu | Glu | Val | Ala | Arg | Lys | Asn | Phe | Leu | Glu | Ser | Leu | |
| -60 | | | | -55 | | | | | -50 | | | | | | -45 | |
| AAA | TAT | GTT | GAA | GCT | AAC | AAA | GGT | GCC | ATC | AAC | CAT | TTG | TCC | GAT | TTG | 245 |
| Lys | Tyr | Val | Glu | Ala | Asn | Lys | Gly | Ala | Ile | Asn | His | Leu | Ser | Asp | Leu | |
| | | | | -40 | | | | | -35 | | | | | | -30 | |
| TCA | TTG | GAT | GAA | TTC | AAA | AAC | CGT | TAT | TTG | ATG | AGT | GCT | GAA | GCT | TTT | 293 |
| Ser | Leu | Asp | Glu | Phe | Lys | Asn | Arg | Tyr | Leu | Met | Ser | Ala | Glu | Ala | Phe | |
| | | | -25 | | | | | -20 | | | | | -15 | | | |
| GAA | CAA | CTC | AAA | ACT | CAA | TTC | GAT | TTG | AAT | GCC | GAA | ACA | AGC | GCT | TGC | 341 |
| Glu | Gln | Leu | Lys | Thr | Gln | Phe | Asp | Leu | Asn | Ala | Glu | Thr | Ser | Ala | Cys | |
| | | -10 | | | | | -5 | | | | | -1 | 1 | | | |
| CGT | ATC | AAT | TCG | GTT | AAC | GTT | CCA | TCG | GAA | TTG | GAT | TTA | CGA | TCA | CTG | 389 |
| Arg | Ile | Asn | Ser | Val | Asn | Val | Pro | Ser | Glu | Leu | Asp | Leu | Arg | Ser | Leu | |
| 5 | | | | | 10 | | | | | 15 | | | | | 20 | |
| CGA | ACT | GTC | ACT | CCA | ATC | CGT | ATG | CAA | GGA | GGC | TGT | GGT | TCA | TGT | TGG | 437 |
| Arg | Thr | Val | Thr | Pro | Ile | Arg | Met | Gln | Gly | Gly | Cys | Gly | Ser | Cys | Trp | |
| | | | | 25 | | | | | 30 | | | | | 35 | | |
| GCT | TTC | TCT | GGT | GTT | GCC | GCA | ACT | GAA | TCA | GCT | TAT | TTG | GCC | TAC | CGT | 485 |
| Ala | Phe | Ser | Gly | Val | Ala | Ala | Thr | Glu | Ser | Ala | Tyr | Leu | Ala | Tyr | Arg | |
| | | | 40 | | | | | 45 | | | | | 50 | | | |
| AAC | ACG | TCT | TTG | GAT | CTT | TCT | GAA | CAG | GAA | CTC | GTC | GAT | TGC | GCA | TCT | 533 |
| Asn | Thr | Ser | Leu | Asp | Leu | Ser | Glu | Gln | Glu | Leu | Val | Asp | Cys | Ala | Ser | |
| | | 55 | | | | | 60 | | | | | 65 | | | | |
| CAA | CAC | GGA | TGT | CAC | GGC | GAT | ACA | ATA | CCA | AGA | GGC | ATC | GAA | TAC | ATC | 581 |
| Gln | His | Gly | Cys | His | Gly | Asp | Thr | Ile | Pro | Arg | Gly | Ile | Glu | Tyr | Ile | |
| | 70 | | | | | 75 | | | | | 80 | | | | | |
| CAA | CAA | AAT | GGT | GTC | GTT | GAA | GAA | AGA | AGC | TAT | CCA | TAC | GTT | GCA | CGA | 629 |
| Gln | Gln | Asn | Gly | Val | Val | Glu | Glu | Arg | Ser | Tyr | Pro | Tyr | Val | Ala | Arg | |
| 85 | | | | | 90 | | | | | 95 | | | | | 100 | |
| GAA | CAA | CGA | TGC | CGA | CGA | CCA | AAT | TCG | CAA | CAT | TAC | GGT | ATC | TCA | AAC | 677 |
| Glu | Gln | Arg | Cys | Arg | Arg | Pro | Asn | Ser | Gln | His | Tyr | Gly | Ile | Ser | Asn | |
| | | | | 105 | | | | | 110 | | | | | 115 | | |
| TAC | TGC | CAA | ATT | TAT | CCA | CCA | GAT | GTG | AAA | CAA | ATC | CGT | GAA | GCT | TTG | 725 |
| Tyr | Cys | Gln | Ile | Tyr | Pro | Pro | Asp | Val | Lys | Gln | Ile | Arg | Glu | Ala | Leu | |
| | | | 120 | | | | | 125 | | | | | 130 | | | |
| ACT | CAA | ACA | CAC | ACA | GCT | ATT | GCC | GTC | ATT | ATT | GGC | ATC | AAA | GAT | TTG | 773 |
| Thr | Gln | Thr | His | Thr | Ala | Ile | Ala | Val | Ile | Ile | Gly | Ile | Lys | Asp | Leu | |
| | | 135 | | | | | 140 | | | | | 145 | | | | |
| AGA | GCT | TTC | CAA | CAT | TAT | GAT | GGA | CGA | ACA | ATC | ATT | CAA | CAT | GAC | AAT | 821 |
| Arg | Ala | Phe | Gln | His | Tyr | Asp | Gly | Arg | Thr | Ile | Ile | Gln | His | Asp | Asn | |
| 150 | | | | | 155 | | | | | 160 | | | | | | |
| GGT | TAT | CAA | CCA | AAC | TAT | CAT | GCC | GTC | AAC | ATT | GTC | GGT | TAC | GGA | AGT | 869 |
| Gly | Tyr | Gln | Pro | Asn | Tyr | His | Ala | Val | Asn | Ile | Val | Gly | Tyr | Gly | Ser | |
| 165 | | | | | 170 | | | | | 175 | | | | | 180 | |
| ACA | CAA | GGC | GAC | GAT | TAT | TGG | ATC | GTA | CGA | AAC | AGT | TGG | GAT | ACT | ACC | 917 |
| Thr | Gln | Gly | Asp | Asp | Tyr | Trp | Ile | Val | Arg | Asn | Ser | Trp | Asp | Thr | Thr | |
| | | | | 185 | | | | | 190 | | | | | 195 | | |
| TGG | GGA | GAT | AGC | GGA | TAC | GGA | TAT | TTC | CAA | GCC | GGA | AAC | AAC | CTC | ATG | 965 |
| Trp | Gly | Asp | Ser | Gly | Tyr | Gly | Tyr | Phe | Gln | Ala | Gly | Asn | Asn | Leu | Met | |
| | | | 200 | | | | | 205 | | | | | 210 | | | |
| ATG | ATC | GAA | CAA | TAT | CCA | TAT | GTT | GTA | ATC | ATG | TGAACATTTG | | AAATTGAATA | | | 1018 |
| Met | Ile | Glu | Gln | Tyr | Pro | Tyr | Val | Val | Ile | Met | | | | | | |
| | | 215 | | | | | 220 | | | | | | | | | |
| TATTTATTTG | | TTTTCAAAAT | | AAAAACAACT | | ACTCTTGCGA | | GTATTTTTA | | CTCG | | | | | | 1072 |

( 2 ) INFORMATION FOR SEQ ID NO:6:

( i ) SEQUENCE CHARACTERISTICS:
    ( A ) LENGTH: 321 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Met   Lys   Phe   Val   Leu   Ala   Ile   Ala   Ser   Leu   Leu   Val   Leu   Ser   Thr   Val
-98         -95                           -90                           -85

Tyr   Ala   Arg   Pro   Ala   Ser   Ile   Lys   Thr   Phe   Glu   Glu   Phe   Lys   Lys   Ala
            -80                     -75                     -70

Phe   Asn   Lys   Asn   Tyr   Ala   Thr   Val   Glu   Glu   Glu   Val   Ala   Arg   Lys
-65                           -60                     -55

Asn   Phe   Leu   Glu   Ser   Leu   Lys   Tyr   Val   Glu   Ala   Asn   Lys   Gly   Ala   Ile
-50                           -45                     -40                                 -35

Asn   His   Leu   Ser   Asp   Leu   Ser   Leu   Asp   Glu   Phe   Lys   Asn   Arg   Tyr   Leu
                  -30                           -25                                 -20

Met   Ser   Ala   Glu   Ala   Phe   Glu   Gln   Leu   Lys   Thr   Gln   Phe   Asp   Leu   Asn
                  -15                           -10                           -5

Ala   Glu   Thr   Ser   Ala   Cys   Arg   Ile   Asn   Ser   Val   Asn   Val   Pro   Ser   Glu
      -1    1                       5                       10

Leu   Asp   Leu   Arg   Ser   Leu   Arg   Thr   Val   Thr   Pro   Ile   Arg   Met   Gln   Gly
15                      20                      25                                  30

Gly   Cys   Gly   Ser   Cys   Trp   Ala   Phe   Ser   Gly   Val   Ala   Ala   Thr   Glu   Ser
                  35                            40                            45

Ala   Tyr   Leu   Ala   Tyr   Arg   Asn   Thr   Ser   Leu   Asp   Leu   Ser   Glu   Gln   Glu
                  50                            55                            60

Leu   Val   Asp   Cys   Ala   Ser   Gln   His   Gly   Cys   His   Gly   Asp   Thr   Ile   Pro
            65                            70                            75

Arg   Gly   Ile   Glu   Tyr   Ile   Gln   Gln   Asn   Gly   Val   Val   Glu   Glu   Arg   Ser
      80                            85                            90

Tyr   Pro   Tyr   Val   Ala   Arg   Glu   Gln   Arg   Cys   Arg   Arg   Pro   Asn   Ser   Gln
95                            100                     105                           110

His   Tyr   Gly   Ile   Ser   Asn   Tyr   Cys   Gln   Ile   Tyr   Pro   Pro   Asp   Val   Lys
                        115                           120                           125

Gln   Ile   Arg   Glu   Ala   Leu   Thr   Gln   Thr   His   Thr   Ala   Ile   Ala   Val   Ile
                  130                     135                           140

Ile   Gly   Ile   Lys   Asp   Leu   Arg   Ala   Phe   Gln   His   Tyr   Asp   Gly   Arg   Thr
            145                           150                     155

Ile   Ile   Gln   His   Asp   Asn   Gly   Tyr   Gln   Pro   Asn   Tyr   His   Ala   Val   Asn
      160                     165                           170

Ile   Val   Gly   Tyr   Gly   Ser   Thr   Gln   Gly   Asp   Asp   Tyr   Trp   Ile   Val   Arg
175                     180                     185                                 190

Asn   Ser   Trp   Asp   Thr   Thr   Trp   Gly   Asp   Ser   Gly   Tyr   Gly   Tyr   Phe   Gln
                        195                     200                           205

Ala   Gly   Asn   Asn   Leu   Met   Met   Ile   Glu   Gln   Tyr   Pro   Tyr   Val   Val   Ile
                  210                     215                           220

Met
```

( 2 ) INFORMATION FOR SEQ ID NO:7:

( i ) SEQUENCE CHARACTERISTICS:
    ( A ) LENGTH: 491 base pairs
    ( B ) TYPE: nucleic acid
    ( C ) STRANDEDNESS: single ( D ) TOPOLOGY: linear ( i i ) MOLECULE TYPE: cDNA ( i x ) FEATURE:
  ( A ) NAME/KEY: CDS
  ( B ) LOCATION: 1..390

( x i ) SEQUENCE DESCRIPTION: SEQ ID NO:7:

| GAT | CAA | GTC | GAT | GTT | AAA | GAT | TGT | GCC | AAC | AAT | GAA | ATC | AAA | AAA | GTA | 48 |
| Asp | Gln | Val | Asp | Val | Lys | Asp | Cys | Ala | Asn | Asn | Glu | Ile | Lys | Lys | Val | |
| 1 | | | | 5 | | | | | 10 | | | | | 15 | | |

| ATG | GTC | GAT | GGT | TGC | CAT | GGT | TCT | GAT | CCA | TGC | ATA | ATC | CAT | CGT | GGT | 96 |
| Met | Val | Asp | Gly | Cys | His | Gly | Ser | Asp | Pro | Cys | Ile | Ile | His | Arg | Gly | |
| | | | 20 | | | | | 25 | | | | | 30 | | | |

| AAA | CCA | TTC | ACT | TTG | GAA | GCC | TTA | TTC | GAT | GCC | AAC | CAA | AAC | ACT | AAA | 144 |
| Lys | Pro | Phe | Thr | Leu | Glu | Ala | Leu | Phe | Asp | Ala | Asn | Gln | Asn | Thr | Lys | |
| | | | 35 | | | | | 40 | | | | | 45 | | | |

| ACC | GCT | AAA | ACT | GAA | ATC | AAA | GCC | AGC | CTC | GAT | GGT | CTT | GAA | ATT | GAT | 192 |
| Thr | Ala | Lys | Thr | Glu | Ile | Lys | Ala | Ser | Leu | Asp | Gly | Leu | Glu | Ile | Asp | |
| | 50 | | | | | 55 | | | | | 60 | | | | | |

| GTT | CCC | GGT | ATT | GAT | ACC | AAT | GCT | TGC | CAT | TTT | ATG | AAA | TGT | CCA | TTG | 240 |
| Val | Pro | Gly | Ile | Asp | Thr | Asn | Ala | Cys | His | Phe | Met | Lys | Cys | Pro | Leu | |
| 65 | | | | | 70 | | | | | 75 | | | | | 80 | |

| GTT | AAA | GGT | CAA | CAA | TAT | GAT | GCC | AAA | TAT | ACA | TGG | AAT | GTG | CCC | AAA | 288 |
| Val | Lys | Gly | Gln | Gln | Tyr | Asp | Ala | Lys | Tyr | Thr | Trp | Asn | Val | Pro | Lys | |
| | | | | 85 | | | | | 90 | | | | | 95 | | |

| ATT | GCA | CCA | AAA | TCT | GAA | AAC | GTT | GTC | GTT | ACA | GTC | AAA | CTT | GTT | GGT | 336 |
| Ile | Ala | Pro | Lys | Ser | Glu | Asn | Val | Val | Val | Thr | Val | Lys | Leu | Val | Gly | |
| | | | 100 | | | | | 105 | | | | | 110 | | | |

| GAT | AAT | GGT | GTT | TTG | GCT | TGC | GCT | ATT | GCT | ACC | CAC | GCT | AAA | ATC | CGT | 384 |
| Asp | Asn | Gly | Val | Leu | Ala | Cys | Ala | Ile | Ala | Thr | His | Ala | Lys | Ile | Arg | |
| | | 115 | | | | | 120 | | | | | 125 | | | | |

| GAT | TAAAAAAAAA | AAATAAATAT | GAAATTTTC | ACCAACATCG | AACAAAATTC | | | | | | | | | | | 437 |
| Asp | | | | | | | | | | | | | | | | |
| 130 | | | | | | | | | | | | | | | | |

AATAACCAAA ATTTGAATCA AAAACGGAAT TCCAAGCTGA GCGCCGGTCG CTAC     491

( 2 ) INFORMATION FOR SEQ ID NO:8:

( i ) SEQUENCE CHARACTERISTICS:
    ( A ) LENGTH: 129 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

| Asp | Gln | Val | Asp | Val | Lys | Asp | Cys | Ala | Asn | Asn | Glu | Ile | Lys | Lys | Val |
| 1 | | | | 5 | | | | | 10 | | | | | 15 | |

| Met | Val | Asp | Gly | Cys | His | Gly | Ser | Asp | Pro | Cys | Ile | Ile | His | Arg | Gly |
| | | | 20 | | | | | 25 | | | | | 30 | | |

| Lys | Pro | Phe | Thr | Leu | Glu | Ala | Leu | Phe | Asp | Ala | Asn | Gln | Asn | Thr | Lys |
| | | | 35 | | | | | 40 | | | | | 45 | | |

| Thr | Ala | Lys | Thr | Glu | Ile | Lys | Ala | Ser | Leu | Asp | Gly | Leu | Glu | Ile | Asp |
| | 50 | | | | | 55 | | | | | 60 | | | | |

| Val | Pro | Gly | Ile | Asp | Thr | Asn | Ala | Cys | His | Phe | Met | Lys | Cys | Pro | Leu |
| 65 | | | | | 70 | | | | | 75 | | | | | 80 |

| Val | Lys | Gly | Gln | Gln | Tyr | Asp | Ala | Lys | Tyr | Thr | Trp | Asn | Val | Pro | Lys |
| | | | | 85 | | | | | 90 | | | | | 95 | |

| Ile | Ala | Pro | Lys | Ser | Glu | Asn | Val | Val | Val | Thr | Val | Lys | Leu | Val | Gly |

```
                    100                         105                         110
Asp  Asn  Gly  Val  Leu  Ala  Cys  Ala  Ile  Ala  Thr  His  Ala  Lys  Ile  Arg
               115                         120                         125
Asp
```

( 2 ) INFORMATION FOR SEQ ID NO:9:

( i ) SEQUENCE CHARACTERISTICS:
        ( A ) LENGTH: 1172 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..738

( x i ) SEQUENCE DESCRIPTION: SEQ ID NO:9:

```
GAATTCCTTT  TTTTTCTTT  CTCTCTCTAA  AATCTAAAAT  CCATCCAAC  ATG  AAA  ATT          58
                                                         Met  Lys  Ile
                                                         -98

GTT  TTG  GCC  ATC  GCC  TCA  TTG  TTG  GCA  TTG  AGC  GCT  GTT  TAT  GCT  CGT  106
Thr  Leu  Ala  Ile  Ala  Ser  Leu  Leu  Ala  Leu  Ser  Ala  Val  Tyr  Ala  Arg
-95                       -90                      -85                     -80

CCA  TCA  TCG  ATC  AAA  ACT  TTT  GAA  GAA  TAC  AAA  AAA  GCC  TTC  AAC  AAA  154
Pro  Ser  Ser  Ile  Lys  Thr  Phe  Glu  Glu  Tyr  Lys  Lys  Ala  Phe  Asn  Lys
                    -75                      -70                      -65

AGT  TAT  GCT  ACC  TTC  GAA  GAT  CAA  GAA  GCT  GCC  CGT  AAA  AAC  TTT  TTG  202
Ser  Tyr  Ala  Thr  Phe  Glu  Asp  Gln  Glu  Ala  Ala  Arg  Lys  Asn  Phe  Leu
               -60                      -55                      -50

GAA  TCA  GTA  AAA  TAT  GTT  CAA  TCA  AAT  GGA  GGT  GCC  ATC  AAC  CAT  TTG  250
Glu  Ser  Val  Lys  Tyr  Val  Gln  Ser  Asn  Gly  Gly  Ala  Ile  Asn  His  Leu
          -45                      -40                      -35

TCC  GAT  TTG  TCG  TTG  GAT  GAA  TTC  AAA  AAC  CGA  TTT  TTG  ATG  AGT  GCA  298
Ser  Asp  Leu  Ser  Leu  Asp  Glu  Phe  Lys  Asn  Arg  Phe  Leu  Met  Ser  Ala
     -30                      -25                      -20

GAA  GCT  TTT  GAA  CAC  CTC  AAA  ACT  CAA  TTC  GAT  TTG  AAT  GCT  GAA  ACT  346
Glu  Ala  Phe  Glu  His  Leu  Lys  Thr  Gln  Phe  Asp  Leu  Asn  Ala  Glu  Thr
-15                      -10                       -5                      -1    1

AAC  GCC  TGC  AGT  ATC  AAT  GGA  AAT  GCT  CCA  GCT  GAA  ATC  GAT  TTG  CGA  394
Asn  Ala  Cys  Ser  Ile  Asn  Gly  Asn  Ala  Pro  Ala  Glu  Ile  Asp  Leu  Arg
               5                        10                       15

CAA  ATG  CGA  ACT  GTC  ACT  CCC  ATT  CGT  ATG  CAA  GGA  GGC  TGT  GGT  TCA  442
Gln  Met  Arg  Thr  Val  Thr  Pro  Ile  Arg  Met  Gln  Gly  Gly  Cys  Gly  Ser
          20                       25                       30

TGT  TGG  GCT  TTC  TCT  GGT  GTT  GCC  GCA  ACT  GAA  TCA  GCT  TAT  TTG  GCT  490
Cys  Trp  Ala  Phe  Ser  Gly  Val  Ala  Ala  Thr  Glu  Ser  Ala  Tyr  Leu  Ala
     35                       40                       45

CAC  CGT  AAT  CAA  TCA  TTG  GAT  CTT  GCT  GAA  CAA  GAA  TTA  GTC  GAT  TGT  538
His  Arg  Asn  Gln  Ser  Leu  Asp  Leu  Ala  Glu  Gln  Glu  Leu  Val  Asp  Cys
50                       55                       60                       65

GCT  TCC  CAA  CAC  GGT  TGT  CAT  GGT  GAT  ACC  ATT  CCA  CGT  GGT  ATT  GAA  586
Ala  Ser  Gln  His  Gly  Cys  His  Gly  Asp  Thr  Ile  Pro  Arg  Gly  Ile  Glu
               70                       75                       80

TAC  ATC  CAA  CAT  AAT  GGT  GTC  GTC  CAA  GAA  AGC  TAC  TAT  CGA  TAC  GTT  634
Tyr  Ile  Gln  His  Asn  Gly  Val  Val  Gln  Glu  Ser  Tyr  Tyr  Arg  Tyr  Val
          85                       90                       95

GCA  CGA  GAA  CAA  TCA  TGC  CGA  CGA  CCA  AAT  GCA  CAA  CGT  TTC  GGT  ATC  682
Ala  Arg  Glu  Gln  Ser  Cys  Arg  Arg  Pro  Asn  Ala  Gln  Arg  Phe  Gly  Ile
          100                      105                      110
```

```
TCA  AAC  TAT  TGC  CAA  ATT  TAC  CCA  CCA  AAT  GCA  AAC  AAA  ATT  CGT  GAA        730
Ser  Asn  Tyr  Cys  Gln  Ile  Tyr  Pro  Pro  Asn  Ala  Asn  Lys  Ile  Arg  Glu
115                           120                      125

GCT  TTG  GCT  CAA  ACC  CAC  AGC  GCT  ATT  GCC  GTC  ATT  ATT  GGC  ATC  AAA        778
Ala  Leu  Ala  Gln  Thr  His  Ser  Ala  Ile  Ala  Val  Ile  Ile  Gly  Ile  Lys
130                      135                      140                          145

GAT  TTA  GAC  GCA  TTC  CGT  CAT  TAT  GAT  GGC  CGA  ACA  ATC  ATT  CAA  CGC        826
Asp  Leu  Asp  Ala  Phe  Arg  His  Tyr  Asp  Gly  Arg  Thr  Ile  Ile  Gln  Arg
                    150                      155                           160

GAT  AAT  GGT  TAC  CAA  CCA  AAC  TAT  CAC  GCT  GTC  AAC  ATT  GTT  GGT  TAC        874
Asp  Asn  Gly  Tyr  Gln  Pro  Asn  Tyr  His  Ala  Val  Asn  Ile  Val  Gly  Tyr
               165                      170                      175

AGT  AAC  GCA  CAA  GGT  GTC  GAT  TAT  TGG  ATC  GTA  CGA  AAC  AGT  TGG  GAT        922
Ser  Asn  Ala  Gln  Gly  Val  Asp  Tyr  Trp  Ile  Val  Arg  Asn  Ser  Trp  Asp
               180                      185                      190

ACC  AAT  TGG  GGT  GAT  AAT  GGT  TAC  GGT  TAT  TTT  GCT  GCC  AAC  ATC  GAT        970
Thr  Asn  Trp  Gly  Asp  Asn  Gly  Tyr  Gly  Tyr  Phe  Ala  Ala  Asn  Ile  Asp
          195                      200                      205

TTG  ATG  ATG  ATT  GAA  GAA  TAT  CCA  TAT  GTT  GTC  ATT  CTC  TAAACAAAAA          1019
Leu  Met  Met  Ile  Glu  Glu  Tyr  Pro  Tyr  Val  Val  Ile  Leu
210                      215                      220

GACAATTTCT  TATATGATTG  TCACTAATTT  ATTTAAAATC  AAAATTTTTA  GAAAATGAAT              1079

AAATTCATTC  ACAAAATTA   AAAAAAAAAA  AAAAAAAAAA  AAAAAAAAAA  AAAAAAAAAA              1139

AAAAAAAAAA  AAAAAAAAAA  AAAAAAAAA   AAA                                             1172
```

( 2 ) INFORMATION FOR SEQ ID NO:10:

( i ) SEQUENCE CHARACTERISTICS:
        ( A ) LENGTH: 320 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Lys  Ile  Thr  Leu  Ala  Ile  Ala  Ser  Leu  Leu  Ala  Leu  Ser  Ala  Val
-98       -95                      -90                      -85

Tyr  Ala  Arg  Pro  Ser  Ser  Ile  Lys  Thr  Phe  Glu  Glu  Tyr  Lys  Lys  Ala
          -80                 -75                      -70

Phe  Asn  Lys  Ser  Tyr  Ala  Thr  Phe  Glu  Asp  Glu  Glu  Ala  Ala  Arg  Lys
     -65                      -60                 -55

Asn  Phe  Leu  Glu  Ser  Val  Lys  Tyr  Val  Gln  Ser  Asn  Gly  Gly  Ala  Ile
-50                      -45                 -40                           -35

Asn  His  Leu  Ser  Asp  Leu  Ser  Leu  Asp  Glu  Phe  Lys  Asn  Arg  Phe  Leu
               -30                      -25                      -20

Met  Ser  Ala  Glu  Ala  Phe  Glu  His  Leu  Lys  Thr  Gln  Phe  Asp  Leu  Asn
               -15                      -10                      -5

Ala  Glu  Thr  Asn  Ala  Cys  Ser  Ile  Asn  Gly  Asn  Ala  Pro  Ala  Glu  Ile
     -1   1                     5                       10

Asp  Leu  Arg  Gln  Met  Arg  Thr  Val  Thr  Pro  Ile  Arg  Met  Gln  Gly  Gly
15                      20                 25                            30

Cys  Gly  Ser  Cys  Trp  Ala  Phe  Ser  Gly  Val  Ala  Ala  Thr  Glu  Ser  Ala
                    35                 40                      45

Tyr  Leu  Ala  His  Arg  Asn  Gln  Ser  Leu  Asp  Leu  Ala  Glu  Gln  Glu  Leu
               50                      55                      60

Val  Asp  Cys  Ala  Ser  Gln  His  Gly  Cys  His  Gly  Asp  Thr  Ile  Pro  Arg
               65                      70                 75

Gly  Ile  Glu  Tyr  Ile  Gln  His  Asn  Gly  Val  Val  Gln  Glu  Ser  Tyr  Tyr
```

-continued

|     |     |     |     |     | 80  |     |     |     |     | 85  |     |     |     |     | 90  |     |     |     |     |
|-----|-----|-----|-----|-----|-----|-----|-----|-----|-----|-----|-----|-----|-----|-----|-----|-----|-----|-----|-----|
| Arg | Tyr | Val | Ala | Arg | Glu | Gln | Ser | Cys | Arg | Arg | Pro | Asn | Ala | Gln | Arg |
| 95  |     |     |     |     | 100 |     |     |     |     | 105 |     |     |     |     | 110 |
| Phe | Gly | Ile | Ser | Asn | Tyr | Cys | Gln | Ile | Tyr | Pro | Pro | Asn | Ala | Asn | Lys |
|     |     |     |     | 115 |     |     |     |     | 120 |     |     |     |     | 125 |     |
| Ile | Arg | Glu | Ala | Leu | Ala | Gln | Thr | His | Ser | Ala | Ile | Ala | Val | Ile | Ile |
|     |     |     | 130 |     |     |     |     | 135 |     |     |     |     | 140 |     |     |
| Gly | Ile | Lys | Asp | Leu | Asp | Ala | Phe | Arg | His | Tyr | Asp | Gly | Arg | Thr | Ile |
|     |     | 145 |     |     |     |     | 150 |     |     |     |     | 155 |     |     |     |
| Ile | Gln | Arg | Asp | Asn | Gly | Tyr | Gln | Pro | Asn | Tyr | His | Ala | Val | Asn | Ile |
|     | 160 |     |     |     |     | 165 |     |     |     |     | 170 |     |     |     |     |
| Val | Gly | Tyr | Ser | Asn | Ala | Gln | Gly | Val | Asp | Tyr | Trp | Ile | Val | Arg | Asn |
| 175 |     |     |     |     | 180 |     |     |     |     | 185 |     |     |     |     | 190 |
| Ser | Trp | Asp | Thr | Asn | Trp | Gly | Asp | Asn | Gly | Tyr | Gly | Tyr | Phe | Ala | Ala |
|     |     |     |     | 195 |     |     |     |     | 200 |     |     |     |     | 205 |     |
| Asn | Ile | Asp | Leu | Met | Met | Ile | Glu | Glu | Tyr | Pro | Tyr | Val | Val | Ile | Leu |
|     |     |     |     | 210 |     |     |     |     | 215 |     |     |     |     | 220 |     |

( 2 ) INFORMATION FOR SEQ ID NO:11:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( i x ) FEATURE:
        ( A ) NAME/KEY: misc feature
        ( B ) LOCATION: 50
        ( D ) OTHER INFORMATION: /label=Xaa is His or Tyr ( i x ) FEATURE:
        ( A ) NAME/KEY: misc feature
        ( B ) LOCATION: 81
        ( D ) OTHER INFORMATION: /label=Xaa is Glu or Lys ( i x ) FEATURE:
        ( A ) NAME/KEY: misc feature
        ( B ) LOCATION: 124
        ( D ) OTHER INFORMATION: /label=Xaa is Ala or Val ( i x ) FEATURE:
        ( A ) NAME/KEY: misc feature
        ( B ) LOCATION: 136
        ( D ) OTHER INFORMATION: /label=Xaa is Ser or Thr ( i x ) FEATURE:
        ( A ) NAME/KEY: misc feature
        ( B ) LOCATION: 215
        ( D ) OTHER INFORMATION: /label=Xaa is Glu or Gln ( x i ) SEQUENCE DESCRIPTION: SEQ ID NO:11:

| Thr | Asn | Ala | Cys | Ser | Ile | Asn | Gly | Asn | Ala | Pro | Ala | Glu | Ile | Asp | Leu |
| 1   |     |     |     | 5   |     |     |     |     | 10  |     |     |     |     | 15  |     |
| Arg | Gln | Met | Arg | Thr | Val | Thr | Pro | Ile | Arg | Met | Gln | Gly | Gly | Cys | Gly |
|     |     |     | 20  |     |     |     |     | 25  |     |     |     |     | 30  |     |     |
| Ser | Cys | Trp | Ala | Phe | Ser | Gly | Val | Ala | Ala | Thr | Glu | Ser | Ala | Tyr | Leu |
|     |     |     | 35  |     |     |     |     | 40  |     |     |     |     | 45  |     |     |
| Ala | Xaa | Arg | Asn | Gln | Ser | Leu | Asp | Leu | Ala | Glu | Gln | Glu | Leu | Val | Asp |
|     | 50  |     |     |     |     | 55  |     |     |     |     | 60  |     |     |     |     |
| Cys | Ala | Ser | Gln | His | Gly | Cys | His | Gly | Asp | Thr | Ile | Pro | Arg | Gly | Ile |
| 65  |     |     |     |     | 70  |     |     |     |     | 75  |     |     |     |     | 80  |
| Xaa | Tyr | Ile | Gln | His | Asn | Gly | Val | Val | Gln | Glu | Ser | Tyr | Tyr | Arg | Tyr |
|     |     |     |     | 85  |     |     |     |     | 90  |     |     |     |     | 95  |     |

Val Ala Arg Glu Gln Ser Cys Arg Arg Pro Asn Ala Gln Arg Phe Gly
                100                 105                 110

Ile Ser Asn Tyr Cys Gln Ile Tyr Pro Pro Asn Xaa Asn Lys Ile Arg
            115                 120                 125

Glu Ala Leu Ala Gln Thr His Xaa Ala Ile Ala Val Ile Ile Gly Ile
        130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
        195                 200                 205

Asp Leu Met Met Ile Glu Xaa Tyr Pro Tyr Val Val Ile Leu
210                 215                 220

( 2 ) INFORMATION FOR SEQ ID NO:12:

( i ) SEQUENCE CHARACTERISTICS:
         ( A ) LENGTH: 129 amino acids
         ( B ) TYPE: amino acid
         ( D ) TOPOLOGY: linear ( i i ) MOLECULE TYPE: protein ( i x ) FEATURE:
         ( A ) NAME/KEY: misc feature
         ( B ) LOCATION: 47
         ( D ) OTHER INFORMATION: /label=Xaa is Thr or Ser ( i x ) FEATURE:
         ( A ) NAME/KEY: misc feature
         ( B ) LOCATION: 114
         ( D ) OTHER INFORMATION: /label=Xaa is Asp or Asn ( i x ) FEATURE:
         ( A ) NAME/KEY: misc feature
         ( B ) LOCATION: 127
         ( D ) OTHER INFORMATION: /label=Xaa is Ile or Leu ( x i ) SEQUENCE DESCRIPTION: SEQ ID NO:12:

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Xaa Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Val Met Gly
            100                 105                 110

Asp Xaa Gly Val Leu Ala Cys Ala Ile Ala Thr His Ala Lys Xaa Arg
        115                 120                 125

Asp ( 2 ) INFORMATION FOR SEQ ID NO:13:

( i ) SEQUENCE CHARACTERISTICS:
  ( A ) LENGTH: 129 amino acids
  ( B ) TYPE: amino acid
  ( D ) TOPOLOGY: linear ( i i ) MOLECULE TYPE: protein ( i x ) FEATURE:
  ( A ) NAME/KEY: misc feature
  ( B ) LOCATION: 11
  ( D ) OTHER INFORMATION: /label=Xaa is Asn or Ser ( i x ) FEATURE:
  ( A ) NAME/KEY: misc feature
  ( B ) LOCATION: 52
  ( D ) OTHER INFORMATION: /label=Xaa is Thr or Ile ( i x ) FEATURE:
  ( A ) NAME/KEY: misc feature
  ( B ) LOCATION: 54
  ( D ) OTHER INFORMATION: /label=Xaa is Ile or Thr ( i x ) FEATURE:
  ( A ) NAME/KEY: misc feature
  ( B ) LOCATION: 76
  ( D ) OTHER INFORMATION: /label=Xaa is Met or Val ( i x ) FEATURE:
  ( A ) NAME/KEY: misc feature
  ( B ) LOCATION: 88
  ( D ) OTHER INFORMATION: /label=Xaa is Ala or Ile ( i x ) FEATURE:
  ( A ) NAME/KEY: misc feature
  ( B ) LOCATION: 111
  ( D ) OTHER INFORMATION: /label=Xaa is Val or Ile ( x i ) SEQUENCE DESCRIPTION: SEQ ID NO:13:

Asp Gln Val Asp Val Lys Asp Cys Ala Asn Xaa Glu Ile Lys Lys Val
 1               5                   10                  15
Met Val Asp Gly Cys His Gly Ser Asp Pro Cys Ile Ile His Arg Gly
                20                  25                  30
Lys Pro Phe Thr Leu Glu Ala Leu Phe Asp Ala Asn Gln Asn Thr Lys
            35                  40                  45
Thr Ala Lys Xaa Glu Xaa Lys Ala Ser Leu Asp Gly Leu Glu Ile Asp
        50              55                  60
Val Pro Gly Ile Asp Thr Asn Ala Cys His Phe Xaa Lys Cys Pro Leu
65                  70                  75                  80
Val Lys Gly Gln Gln Tyr Asp Xaa Lys Tyr Thr Trp Asn Val Pro Lys
                85                  90                  95
Ile Ala Pro Lys Ser Glu Asn Val Val Thr Val Lys Leu Xaa Gly
                100                 105                 110
Asp Asn Gly Val Leu Ala Cys Ala Ile Ala Thr His Ala Lys Ile Arg
            115                 120                 125
Asp